United States Patent [19]
Sawhney et al.

[11] Patent Number: 6,051,248
[45] Date of Patent: *Apr. 18, 2000

[54] COMPLIANT TISSUE SEALANTS

[75] Inventors: Amapreet S. Sawhney, Lexington; Michelle D. Lyman, Chelmsford; Peter K. Jarrett; Ronald S. Rudowsky, both of Sudbury, all of Mass.

[73] Assignee: Focal, Inc., Lexington, Mass.

[*] Notice: This patent is subject to a terminal disclaimer.

[21] Appl. No.: 09/288,207

[22] Filed: Apr. 8, 1999

Related U.S. Application Data

[63] Continuation of application No. 08/710,689, Sep. 23, 1996, Pat. No. 5,900,245, which is a continuation-in-part of application No. PCT/US96/03834, Mar. 22, 1996.

[51] Int. Cl.$^7$ .............................. C09D 4/00; A61L 25/00; A61L 27/00; A61L 29/00
[52] U.S. Cl. ......................... 424/426; 424/489; 424/490; 528/354; 528/361; 128/898; 128/899; 525/54.1; 525/54.2; 525/408; 525/413; 525/415; 514/772.1
[58] Field of Search ..................................... 424/426, 489, 424/490; 528/354, 361; 128/898, 899; 525/54.1, 54.2, 408, 413, 415; 514/772.1

[56] References Cited

U.S. PATENT DOCUMENTS

| | | |
|---|---|---|
| 3,223,083 | 12/1965 | Cobey . |
| 3,438,374 | 4/1969 | Falb et al. . |
| 3,552,986 | 1/1971 | Bassemir et al. . |
| 3,939,049 | 2/1976 | Ratner et al. . |
| 4,179,304 | 12/1979 | Rossomando . |
| 4,303,066 | 12/1981 | D'Andrea . |
| 4,354,487 | 10/1982 | Oczkowski et al. . |
| 4,511,478 | 4/1985 | Nowinski et al. . |
| 4,741,872 | 5/1988 | De Luca et al. . |
| 4,768,523 | 9/1988 | Cahalan et al. . |
| 4,804,691 | 2/1989 | English et al. . |
| 4,826,945 | 5/1989 | Cohn et al. . |
| 4,846,165 | 7/1989 | Hare et al. . |
| 4,938,763 | 7/1990 | Dunn et al. . |
| 4,997,722 | 3/1991 | Adler . |
| 5,009,224 | 4/1991 | Cole . |
| 5,019,100 | 5/1991 | Hennink et al. . |
| 5,067,961 | 11/1991 | Kelman et al. . |
| 5,100,992 | 3/1992 | Cohn et al. . |
| 5,104,957 | 4/1992 | Kelman et al. . |
| 5,137,800 | 8/1992 | Neckers et al. . |
| 5,147,698 | 9/1992 | Cole . |
| 5,156,613 | 10/1992 | Sawyer . |
| 5,160,745 | 11/1992 | De Luca et al. . |
| 5,173,301 | 12/1992 | Itoh et al. . |
| 5,177,120 | 1/1993 | Hare et al. . |
| 5,201,764 | 4/1993 | Kelman et al. . |
| 5,209,776 | 5/1993 | Bass et al. . |
| 5,226,877 | 7/1993 | Epstein . |
| 5,278,200 | 1/1994 | Coury et al. . |
| 5,296,627 | 3/1994 | Tang et al. . |
| 5,308,887 | 5/1994 | Ko et al. . |
| 5,332,475 | 7/1994 | Mechanic . |
| 5,332,802 | 7/1994 | Kelman et al. . |
| 5,354,336 | 10/1994 | Kelman et al. . |
| 5,372,585 | 12/1994 | Tiefenbrun et al. . |
| 5,385,606 | 1/1995 | Kowanko . |
| 5,403,626 | 4/1995 | Kim et al. . |
| 5,410,016 | 4/1995 | Hubbell et al. . |
| 5,459,177 | 10/1995 | Miyakoshi et al. . |
| 5,476,515 | 12/1995 | Kelman et al. . |
| 5,480,427 | 1/1996 | Kelman et al. . |
| 5,484,913 | 1/1996 | Stilwell et al. . |
| 5,496,872 | 3/1996 | Constancis et al. . |
| 5,508,317 | 4/1996 | Muller . |
| 5,512,091 | 4/1996 | Steiner . |
| 5,516,825 | 5/1996 | Montador . |
| 5,525,647 | 6/1996 | Eichmiller . |
| 5,527,864 | 6/1996 | Suggs et al. . |
| 5,529,914 | 6/1996 | Hubbell et al. . |
| 5,530,038 | 6/1996 | Yamamoto et al. . |
| 5,531,707 | 7/1996 | Kers el al. . |
| 5,531,709 | 7/1996 | Eykmann et al. . |
| 5,540,677 | 7/1996 | Sinofsky . |
| 5,552,452 | 9/1996 | Khadem et al. . |
| 5,554,665 | 9/1996 | Tateosian et al. . |
| 5,561,157 | 10/1996 | Yu el al. . |
| 5,900,245 | 5/1999 | Sawhney et al. ................. 424/426 |

FOREIGN PATENT DOCUMENTS

| | | |
|---|---|---|
| 0 370 646 A1 | 5/1990 | European Pat. Off. . |
| 0 610 731 A1 | 8/1994 | European Pat. Off. . |
| 0 634 140 A1 | 1/1995 | European Pat. Off. . |
| 0 635 276 A1 | 1/1995 | European Pat. Off. . |
| 2 668 060 A1 | 4/1992 | France . |
| 4402590 | 1/1994 | Germany . |
| 62267762 | 5/1986 | Japan . |
| 5310808 | 5/1993 | Japan . |
| WO 93/17669 | 9/1993 | WIPO . |

OTHER PUBLICATIONS

CHEN & HOFFMAN, "Novel Graft Copolymers Of A Temperature–Sensitive Polymer Grafted To A pH–Sensitive, Bioadhesive Polymer For Controlled Drug Delivery", *21st Annual Meeting Of The Society For Biomaterials* (1995).

CIMA, et al., "Hepatocyte Responses To PEO–Tethered Carbohydrates Depend On Tether Conformation", *21st Annual Meeting Of The Society For Biomaterials* (1995).

CONSTANICS, et al., "Colcys As Surgical Adhesives", *21st Annual Meeting Of The Society For Biomaterials* (1995).

(List continued on next page.)

*Primary Examiner*—Nathan M. Nutter
*Attorney, Agent, or Firm*—Arnall Golden & Gregory, LLP

[57] ABSTRACT

An improved barrier or drug delivery system which is highly adherent to the surface to which it is applied is disclosed, along with methods for making the barrier. In the preferred embodiment, the system is compliant, in that it is capable of conforming to the three dimensional structure of a tissue surface as the tissue bends and deforms during healing processes. The barrier or drug delivery systems is formed as a polymeric coating on tissue surfaces by applied a polymerizable monomer to the surface, and then polymerizing the monomer. The polymerized compliant coating preferably is biodegradable and biocompatible, and can be designed with selected properties of compliancy and elasticity for different surgical and therapeutic applications.

23 Claims, 1 Drawing Sheet

OTHER PUBLICATIONS

DUMANIAN, et al., "A New Photopolymerizable Blood Vessel Glue that Seals Human Vessel Anastomoses Without Augmenting Thrombogenicity," *Plastic and Reconstructive Surgery* 95:901 (1995).

DUPONT, et al., "New Surgical Sealant (Glue) Based On Controlled Oxidized Collagen", *21st Annual Meeting Of The Society For Biomaterials* (1995).

FRENKEL, et al., "A Collagen Bilayer Implant For Articular Cartilage Repair In A Rabbit Model", *21st Annual Meeting Of The Society For Biomaterials* (1995).

GAGNIEU, et al., "Colcys: New Crosslinkable Atelocoliagens: Synthesis And Physico–Chemical Properties Of Highly Grafted Polymers", *21st Annual Meeting Of The Society For Biomaterials* (1995).

GERSHKOVICH, et al., "Post–Surgical Adhesion Prevention With Bioresorbable Gels Of Amine Modified Hyaluronic Acid", *21st Annual Meeting Of The Society For Biomaterials* (1995).

HATA, et al., "Enzymatic Polymerization of 2–Hydroxyethylmethacrylate For Artificial Embolization ", *The Third World Biomaterials Congress*, 301 (1988).

HERBERT, et al., "Polytetramethlene Oxide Blended With Polyurethane Reduces Platelet Adhesion", *21st Annual Meeting Of The Society For Biomaterials* (1995).

HSU, et al., "Study On Aqueous Polymerizations Of Vinyl Monomers Initiated By Metal Oxidant–Chelating Agent Redox Initiators", J. Polymer Science: Part A: Polymer Chem. 31:3213–3222 (1993).

IWATA, et al., "Solidfying Liquid With Novel Initiation System For Detachable Balloon Catheters", Biomaterials 13(13):891–896 (1992).

KOBAYASHI, et al., "Water–curable and biodegradable prepolymers," J. Biom. Mat. Res. 25:1481–1494 (1991).

McPHERSON, et al., "Scaling Analysis Of The Prevention Of Protein Adsorption By Grafted Peo Chains", *21st Annual Meeting Of The Society For Biomaterials* (1995).

MILLER, et al., "Prevention Of Post–Surgical Tendon Adhesions Using Hyaluronic Acid Systems", *21st Annual Meeting Of The Society For Biomaterials* (1995).

MOORE, et al., "An Injectable Biodegradable Drug Delivery System Based On Acrylic Terminated Poly(∈–Caprolactone)", *21st Annual Meeting Of The Society For Biomaterials* (1995).

MOURITZEN, et al., "The Effect Of Fibrin Glueing To Seal Bronchial And Alveolar Leakages After Pulmonary Resections And Decortications", Eur. J. Cardio–thorac Surg. 7:75–80 (1993).

PEMBERTON & JOHNSON, "Polymerization of Vinyl Acetate Using Visible Radiation and a Dye–Reducing Agent Sensitizer," Polymer 25:536 (1984).

PEMBERTON & JOHNSON, "Polymerization of Vinyl Acetate Using Visible Radiation and a Dye–Reducing Agent Sensitizer: 2. Kinetic Studies and Polymerization Mechanism, " Polymer 25:543 (1984).

RIMPLER, "Gluing+A Challenge in Surgery" Int. J. Adhesion and Adhesives 16: 17–20 (1996).

SAWHNEY, et al., "Optimization of photopolymerized bioerodible hydrogel properties for a adhesion prevention, " J. Biomed. Mats. Res. 28–831–838 (1994).

SIERRA, et al., "Skullbase Cerebrospinal Fluid Leakage Control With A Fibrin Composite Tissue Adhesive", *21st Annual Meeting Of The Society For Biomaterials* (1995).

TARDY, et al., "New Surgical Sealant(Glue) Based On Controlled Oxidized Collagen: Design And Physico–Chemical Characterization", *21st Annual Meeting Of The Society For Biomaterials* (1995).

TIOLLIER, et al., "Colcys As Surgical Adhesives: In Vivo Characterization And Biocompatibility", *21st Annual Meeting Of The Society For Biomaterials* (1995).

TIOLLIER , et al., "Novel Developments Of Collagen/ Gelatin Surgical Adhesives For Surgical For Surgical Soft Tissue Applications", *21st Annual Meeting Of The Society For Biomaterials* (1995).

TOMIZAWA, et al., "Polypoxy Compound Cross–Linked Cotton Type Collagen Hemostat", *21st Annual Meeting Of The Society For Biomaterials* (1995).

TRUONG, et al., "In Vivo Conditions For Accelerated Hydrolysis Of Bioabsorbable Fibers", *21st Annual Meeting Of The Society For Biomaterials* (1995).

COMPLIANT TISSUE SEALANTS

This application is a continuation of Ser. No. 08/710,689, filed Sep. 23, 1996 and now U.S. Pat. No. 5,900,245, which application is a continuation-in-part of PCT International Application No. PCT/US 96/03834, filed Mar. 22, 1996, the disclosure of which is incorporated herein.

BACKGROUND OF THE INVENTION

The present invention relates to methods and compositions for improving the adherence of polymer gels to surfaces, particularly tissue surfaces, and for improving the compliance of the materials.

Locally polymerized gels have been used as barriers and drug delivery devices for several medical conditions. Adherence of the formed gel to the tissue can be a problem, especially under surgical conditions, where the tissue surface to be treated is typically wet, and may further be covered with blood, mucus or other secretions. Hubbell and co-workers have described two methods for photopolymerizing gels in contact with tissue surfaces. In U.S. Pat. No. 5,410,016, hereby incorporated by reference, application of biodegradable macromers to tissue, followed by photopolymerization to form a gel, is described. Two methods for photopolymerizing gels are described. In "bulk" polymerization, a suitable photoinitiator and accessory reagents are solubilized or dispersed in a solution of gelling macromers. On application of light, the entire solution volume crosslinks to form a gel which acts as a local barrier or drug depot. These gels have substantial adherence to most surfaces, including tissue surfaces which are merely moist. However, if a confounding layer of fluid is present on the surface when the macromer/initiator solution is applied, then the gel may delaminate from the surface after its formation.

An alternative way of forming a gel layer on a surface, as described in U.S. Ser. No. 08/024,657, which is hereby incorporated herein by reference, is called the "interfacial" method. In this method, the surface to be coated is treated with a photoinitiator which adsorbs or absorbs to the surface. After washing away excess, unabsorbed photoinitiator, a polymerizable macromer solution is applied to the surface. On exposure to light, polymerization is initiated at the surface, and progresses outward into the solution to the limit of diffusion of the photoinitiator-generated radicals during their lifespan. Coating thicknesses of up to about 500 micrometers (microns) are routinely obtained. Since they are in effect "grown" from the tissue surface, such gel layers have excellent adhesion to the tissue surface under difficult conditions, including the presence of thin layers of fluid adherent to the surface. The limited thickness of such interfacial gels is desirable in some circumstances, but represents a major limitation where gels of substantially greater thickness than 500 microns are required, for example, for use in drug delivery, or in forming a thick physical barrier between the tissue surface and its surroundings. In addition to the photopolymerizabie gels described by Hubbell et al. (WO 93/17669) and Sawhney et al., (J. Biomed. Mats. Res. 28, 831–838, 1994), systems for forming drug delivery depots or barriers on surfaces include the polymers described in U.S. Pat. No. 4,938,163 to Dunn, et al., U.S. Pat. Nos. 5,100,992 and 4,826,945 to Cohn et al., U.S. Pat. Nos. 4,741,872 and 5,160,745 to De Luca et al., and U.S. Pat. No. 4,511,478 to Nowinski et al. Use of preformed barrier materials such as Goretex™ membrane (W. L. Gore) has been described in the literature.

Although all of these materials are suitable for application to tissue and other substrates, adhesion is in many cases limited, or in the case of the preformed barrier materials, essentially non-existent.

There are many situations in which the application of a polymeric material, or a polymerizable material followed by polymerization, is the appropriate or preferred method of sealing a tissue or organ to prevent migration of a fluid, such as blood or air, from or into the tissue or organ.

Well-known materials for making such bonds are cyanoacrylate-based adhesives and fibrin glue. Cyanoacrylates are chemically related to familiar domestic adhesives such as "CrazyGlue™". On contact with water, the cyanoacrylate residues spontaneously polymerize. The resulting resins are brittle, poorly biodegradable, and often not biocompatible.

Fibrin glues are typically made by contacting a solution or suspension of the blood protein fibrinogen with an enzyme or other reagent which can crosslink it. Typically, the enzyme thrombin is used, which cleaves the fibrinogen molecule, forming fibrin monomer which then spontaneously polymerizes. This is a natural reaction involved in the formation of blood clots. Fibrin glues often have better adherence to tissues than do cyanoacrylates, and are rapidly biodegraded. However, like cyanoacrylates, they have little flexibility or elasticity once their deposition is complete. A familiar example of a crosslinked fibrin-based material is a scab or an eschar.

Neither fibrin glues nor cyanoacrylates are stretchable, once polymerized. It is believed that this lack of compliance (i.e., high elastic modulus and low elongation at rupture) is an important reason why seals formed with these and related prior-art materials are likely to fail prematurely, especially when the area which is joined or sealed is subject to deformation.

Numerous materials are known and used in medicine which are highly elastic, such as rubber gloves and flexible elastic bandages. However, such materials do not bind tightly to tissue, particularly to moist tissue, which is required if the tissue is to be sealed.

It is therefore an object of the present invention to provide methods and compositions for enhancing the adhesion of polymeric materials to tissue surfaces and other substrates.

It is a further object of the present invention to provide methods and compositions for increasing the thicknesses of polymeric materials which can be "tethered" to a tissue surface or other substrates.

It is a further object of the present invention to provide improved initiator systems for the formation of gels on tissues and other surfaces.

It is a further object of the present invention to provide improved methods and new medical indications for the sealing and coating of tissue.

It is another object of the invention to provide an improved sealing material and method, characterized in that the sealant material is compliant with tissue after its formation, as well as strongly adherent to tissue.

It is a further object of the invention to provide kits for the formation of such compliant sealant materials.

SUMMARY OF THE INVENTION

An improved barrier, coating or drug delivery system which is highly adherent to the surface to which it is applied is disclosed, along with methods for making the barrier. The barriers and coatings formed by polymerization of polymerizable materials on the surface of tissue form barriers or coatings which are compliant with the tissue, as well as adherent, i.e., are capable of conforming to the tissue. The polymerized coatings preferably are biocompatible and biodegradable.

In a preferred embodiment, tissue is stained with a photoinitiator, then the polymer solution or gel in combination with a defined amount of the same or a different photoinitator is applied to the tissue. On exposure to light, the resulting system polymerizes at the surface, giving excellent adherence, and also forms a gel throughout the illuminated volume. Thus a gel barrier or coating of arbitrary thickness can be applied to a surface while maintaining high adherence at the interface. This process is referred to herein as "priming". The polymerizable barrier materials are highly useful for sealing tissue surfaces and junctions against leaks of fluids. In the examples described below, the fluids are air and blood; however, the principle is also applicable to other fluids, including bowel contents, urine, bile, cerebrospinal fluid, vitreous and aqueous humors and other fluids whose migration within a living organism must be contained.

In another embodiment, "priming" can be used to reliably adhere preformed barriers or coatings to tissue or other surfaces, or to adhere tissue surfaces to each other. A first surface and a preformed barrier or coating, or another surface, are prestained with initiator, and a thin layer of polymerizable monomer containing initiator is placed between them. Strong adhesion is obtained between the two surfaces on polymerization of the monomer. In a similar fashion, tissue surfaces can be adhered to each other in repair of wounds and formation of anastomoses.

The priming method is suitable for any mode of polymerization. While especially effective in photopolymerization, chemical or thermal polymerization can also be accomplished by this method. Further, an enhancement of photoinitiation can be achieved by adding suitable redox initiation components to the system, providing a new form of light-controlled chemically accelerated polymerization reaction, especially effective in the presence of blood.

DETAILED DESCRIPTION OF THE INVENTION

Figure 1:
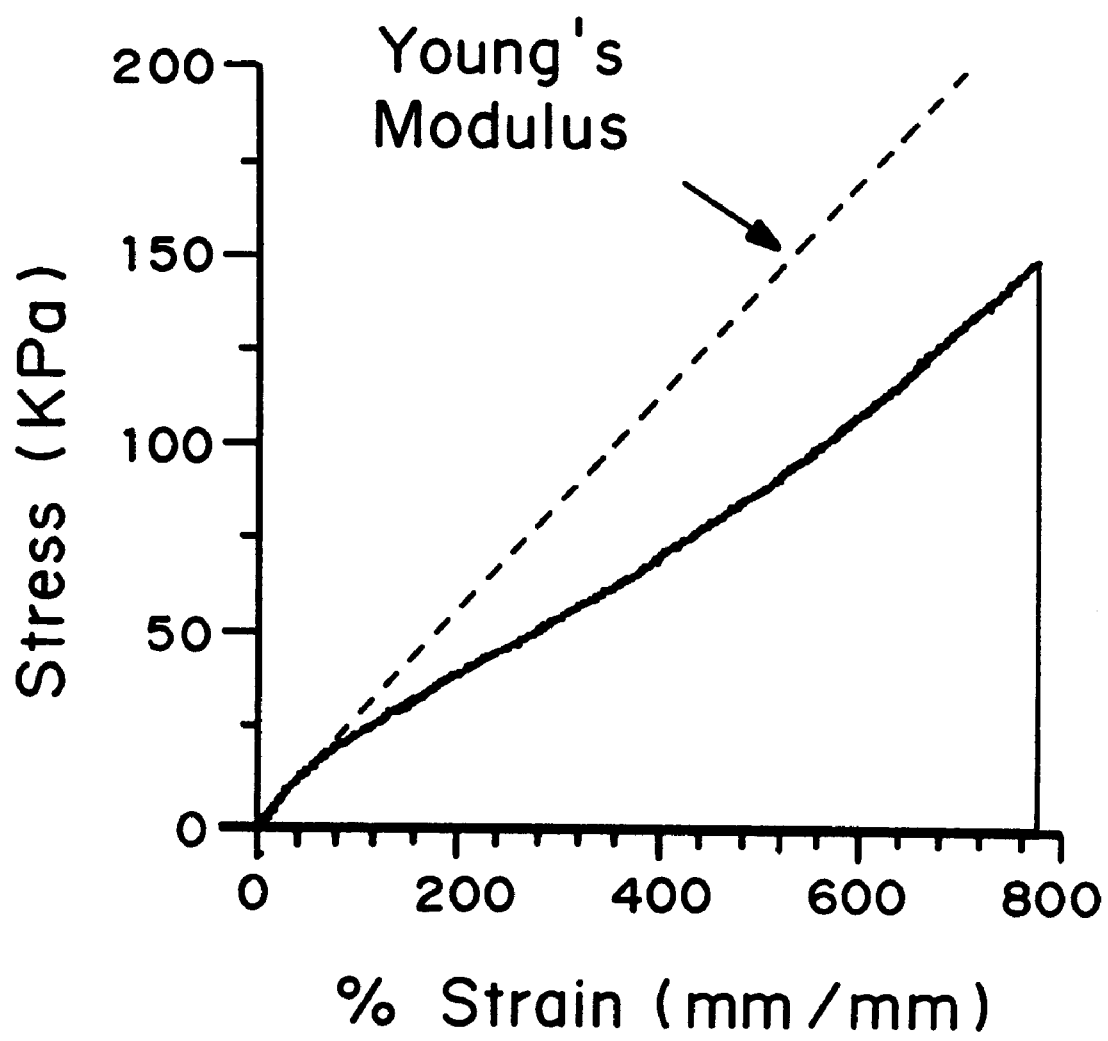
FIG. 1 shows the stress vs. strain curve of a compliant sealant formed by photopolymerization of a poly(ethylene glycol)-oligotrimethylene carbonate copolymer end capped with acrylate ester.

Materials with improved compliance, and methods for their manufacture and application to tissue are provided. In one embodiment, materials may be used which are described in PCT/US/96/03834, filed Mar. 22, 1996, the disclosure of which is incorporated herein by reference. Polymerized barriers or coatings may be formed from polymerizable precursor materials which can include, for example, crosslinkable or curable molecules. A wide variety of precursor materials may be used, provided that they form cured or crosslinked materials having the properties of biocompatibility and an appropriate elastic property, such as a compliance ratio, as described in detail below. Preferably, the polymerized materials are biodegradable. The compliant materials may be used as sealants, may contain biologically active materials, and be used in drug delivery applications.

By selection of the appropriate polymerizable materials, polymeric compliant polymer coatings on tissue may be formed, and the properties of the polymers may be altered to control the normalized compliance ratio of such polymers relative to that of a tissue.

Definitions

As used herein, the term "sealant" refers to a material which decreases or prevents the migration of fluid from or into a surface such as a tissue surface. Sealants are typically formed by the application of precursor molecules to a tissue followed by local polymerization. The same materials may also be used to adhere materials together, either when applied between them and polymerized, or when used to jointly embed materials.

As used herein, the term "biocompatibility," in the context of biologically-related uses, refers to the absence of stimulation of a severe, long-lived or escalating biological response to an implant or coating, and is distinguished from a mild, transient inflammation which typically accompanies surgery or implantation of foreign objects into a living organism.

As used herein the term "biodegradability" refers to the disintegration, which is preferably predictable, of an implant into small entities which will be metabolized or excreted, under the conditions normally present in a living tissue.

The properties of the particular coating or barrier materials disclosed herein are referred to as "materials properties", and include:

the "Young's modulus" (of elasticity) which is the limiting modulus of elasticity extrapolated to zero strain;

the "elastic modulus" which is any modulus of elasticity, not limited to Young's modulus, and may include "secant modulus" and other descriptors of non-linear regions of the stress-strain curve;

the "bulk" or "compressive" modulus which is used in its usual sense of: ratio of stress to a designated compressive strain;

the "elongation at failure" which is the relative strain or extension of a test specimen at which any irreversible or hysteresis-inducing change occurs in the specimen; and the "elongation at break" or "elongation at rupture" which is the relative strain (extension) of a test specimen at which mechanical rupture occurs.

The term "compliance" as used herein is used in a general sense, and refers for example to the ability of an implant to closely match the physiological and mechanical properties of tissues at the implant site, except when "compliance" is used in a specific technical sense as the reciprocal of a modulus.

As applied to a relatively thin, flat material such as a tissue or a layer of sealant, "normalized compliance" (NC) is defined herein as the strain, (i.e., the elongation or compression per unit length of a specimen), divided by the applied force per unit cross-sectional area, further divided by the thickness of the specimen. Hence, for a sample having a width w (for example, the width of the clamps of the testing apparatus), and a thickness t, when an applied force F produces a strain S, then the compliance C is $$C = \frac{S}{F/wt} = \frac{S \cdot wt}{F}$$

and the normalized compliance is $$NC = \frac{C}{t} = \frac{S}{F/w} = \frac{Sw}{F}$$

i.e., the strain in the sample divided by the force per unit width applied to the sample. The normalized compliance allows direct comparison of the forces required to deform the tissue versus a coating on the tissue, without regard to the relative thickness of these materials.

The normalized compliance ratio (abbreviated NCR) is defined as the value of the normalized compliance of the tissue or other substrate divided by the normalized compliance of the sealant material. When both measurements are conducted on strips of the same width and at the same force, the NCR is simply the ratio of the strains at a particular force. A low NCR (less than 1) is obtained when the sealant material is easier to deform than the tissue, while a high NCR (greater than 1) is obtained when the tissue is easier to deform than the sealing material.

As used herein, the term "elastomer" refers to a polymeric material which at room temperature is capable of repeatedly recovering in size and shape after removal of a deforming force. In some embodiments, an elastomer is a material which can be repeatedly stretched to twice its original length and will repeatedly return to its approximate length on release of the stress.

The phrase "elastomeric materials" is a phrase which has been used in the literature. There are many publications describing structure-property relationships of elastomers and other deformable materials. Lower elastic modulus and, frequently, an increased reversible elongation to break or fracture, are found when any of the following occur:

1. The distance between nodes or junctions or more crystalline ("hard") segments increases.
2. The crosslink density decreases. This may be controlled by amount of crosslinker, nature of crosslinker, and degree of cure, as well as by segment length of either the crosslinked species or the crosslinking species, where different.
3. For a material at equilibrium with a continuous phase, an increase in the plasticization of the elastomer by the continuous phase. For applications wherein the continuous phase is water, more particularly physiological saline, increasing hydrophilicity tends to increase compliance.

In order to seal fluid leaks in tissue, the sealing material must remain firmly bonded to the tissue during motions required of the tissue during the healing process. For tissues and organs which cannot be immobilized, such as the lung, an effective sealing material is both tightly-adherent and compliant, having materials properties similar to those of the tissue. Examples of compliant adherent materials and methods for their construction and use are provided.

In one embodiment, one or more initiators are applied to a surface to form an absorbed layer. "Absorbed" is used herein to encompass both "absorbed" and "adsorbed". A solution of polymerizable molecules, referred to herein as "monomers", is then applied.

Methods

In one embodiment, one or more initiators or components of an initiation system are applied directly to the surface, and the unabsorbed excess is optionally removed by washing or blotting. The initiator solution may further contain one or more polymerizable monomers, and other useful formulating ingredients, including accelerators, co-initiators, sensitizers, and co-monomers. Then a liquid containing polymerizable monomers in combination with one or more initiators or components of an initiation system, which may be the same as or different from that absorbed in the first step, is applied. The system, if not self-polymerizing, is then stimulated to polymerize, for example by application of an appropriate wavelength of light.

The priming and monomer-application steps can also be combined. For example, if excess initiator is not removed before monomer addition, then subsequent application of monomer will result in mixture of initiator into the monomer layer. Similarly, if the monomer layer contains an initiator with a high affinity for the surface, then it is possible to apply a monomer layer containing initiator, and wait an appropriate time to allow preferential absorption of the initiator to the surface, to achieve the same effect.

All of these methods may collectively be described as application of the monomer in an "initiating-incorporating manner", encompassing any means of application and mixing which results in both an absorbed layer of initiator, and a layer of monomer incorporating an initiator, being present on a surface to be coated.

The initiators may be chemical, photochemical, or a combination thereof. With non-photochemical systems, a reductant component and an oxidant component may be present in the two parts of the solution, i.e., in the priming layer and the coating layer.

Alternatively, a two-step process can be used to form polymers, especially bioabsorbable hydrogels on tissue. In the first step the tissue is treated with an initiator or a part of an initiator system for the polymerization of olefinic (e.g. acrylic) or other functional monomers, optionally with monomer in the priming solution. This provides an activated tissue surface. In the second step, monomer(s) and, if appropriate, the remainder of an initiator system, are together placed in contact with the activated tissue, resulting in polymerization on the tissue. An example of such a system is the combination of a peroxygen compound in one part, and a reactive ion, such as a transition metal, in another.

This process of spontaneous polymerization does not require the use of a separate energy source. Moreover, since the process of polymerization is initiated when part one contacts part two, there are no "pot life" issues due to initiation of polymerization. If desired, part one or part two can contain dyes or other means for visualizing the hydrogel coating.

An example of a system that can be used in this method is the spontaneous "contact" initiator systems such as those found in two part "acrylic structural adhesives". All components of the materials used as described herein, however, must display biocompatibility as well as the ability to spontaneously polymerize on tissue. The use of tributyl borane for this purpose is illustrated here.

These systems can markedly simplify the delivery of gel to tissue, especially in areas hard to reach or hold for a photochemical system. The delivery system can be much simpler. Moreover, it has been discovered that a two part chemical system such as a redox system and especially one based on peroxygen, can be used to chemically enhance the curing of a photochemical system, thereby combining the control of a photochemical system with the ability of a chemical system to overcome colored impurities, such as blood.

In one embodiment, as described in U.S. Pat. No. 5,410,016, biodegradable macromers are applied to tissue, followed by photopolymerization to form a gel. In addition to the photopolymerizable gels described by Hubbell et al. (WO 93/17669) and Sawhney et al., (*J. Biomed. Mats. Res.,* 28:831–838, 1994), systems for forming drug delivery depots or barriers on surfaces include the polymers described in U.S. Pat. No. 4,938,763 to Dunn et al., U.S. Pat. Nos. 5,100,992 and 4,826,945 to Cohn et al., U.S. Pat. Nos. 4,741,872 and 5,160,745 to De Luca et al., U.S. Pat. No. 5,527,864 to Suggs et al., and U.S. Pat. No. 4,511,478 to Nowinski et al. These materials, which covalently cross-link by free-radical-initiated polymerization, are preferred materials. However, materials which cross-link by other mechanisms, or which comprise low-molecular weight reactive monomers, are also potentially suitable if they are biocompatible and non-toxic.

Compositions

MONOMERS

Any monomer capable of being polymerized to form a surface coating can be used. The monomers may be small molecules, such as acrylic acid or vinyl acetate; or they may be larger molecules containing polymerizable groups, such as acrylate-capped polyethylene glycol (PEG-diacrylate), or other polymers containing ethylenically unsaturated groups, such as those of U.S. Pat. No. 4,938,763 to Dunn et al., U.S. Pat. Nos. 5,100,992 and 4,826,945 to Cohn et al., U.S. Pat. Nos. 4,741,872 and 5,160,745 to De Luca et al., or U.S. Pat. No. 5,410,016 by Hubbell et al. Properties of the monomer, other than polymerizability, will be selected according to the use, using principles as known in the art. There is an extensive literature on the formulation of polymerizable coating materials for particular applications; these formulae can readily be adapted to use the improved adherence-promoting polymerization system described herein with little experimentation.

In the particular application area of coating of tissues, cells, medical devices, and capsules, formation of implants for drug delivery or as mechanical barriers or supports, and other biologically related uses, the general requirement of the coating materials are biocompatibility and lack of toxicity. For all biologically-related uses, toxicity must be low or absent in the finished state for externally coated non-living materials, and at all stages for internally-applied materials. Biocompatibility, in the context of biologically-related uses, is the absence of stimulation of a severe, long-lived or escalating biological response to an implant or coating, and is distinguished from a mild, transient inflammation which accompanies implantation of essentially all foreign objects into a living organism.

The monomer solutions should not contain harmful or toxic solvents. Preferably, the monomers are substantially soluble in water to allow their application in a physiologically-compatible solution, such as buffered isotonic saline. Water-soluble coatings may form thin films, but more preferably form three-dimensional gels of controlled thickness.

It is especially preferable in cases involving implants that the coating formed be biodegradable, so that it does not have to be retrieved from the body. Biodegradability, in this context, is the predictable disintegration of an implant into small molecules which will be metabolized or excreted, under the conditions normally present in a living tissue.

The macro-monomers ("macromers") which are covalently crosslinkable to form hydrogels preferably comprise a block copolymer. The macromers can be quickly polymerized from aqueous solutions. The macromers may advantageously be capable of thermoreversible gelation behavior, and may be polymerized from a solution state or from a gel state.

Preferred monomers are the photopolymerizable, biodegradable, water-soluble macromers described by Hubbell et al. in U.S. Ser. No. 08/022,687, the teachings of which are incorporated herein. These monomers are characterized by having at least two polymerizable groups, separated by at least one degradable region. When polymerized in water, they form coherent gels which persist until eliminated by self-degradation. In the most preferred embodiment, the macromer is formed with a core of a polymer which is water soluble and biocompatible, such as the polyalkylene oxide polyethylene glycol, flanked by hydroxy acids such as lactic acid, having coupled thereto acrylate groups. Preferred monomers, in addition to being biodegradable, biocompatible, and non toxic, will also be at least somewhat elastic after polymerization or curing. Elasticity, or repeatable stretchability, is often exhibited by polymers with low modulus. Brittle polymers, including those formed by polymerization of cyanoacrylates, are not generally effective in contact with biological soft tissue.

It has been determined that monomers with longer distances between crosslinks are generally softer, more compliant, and more elastic. Thus, in the polymers of Hubbell, et al., increased length of the water-soluble segment, such as polyethylene glycol, tends to give more elastic gel, and these tend to adhere better, especially under stretching (as when applied to lung). Molecular weights in the range of 10,000 to 35,000 of polyethylene glycol are preferred for such applications, although ranges from 3,000 to 100,000 are useful.

In the discussion below and the examples, monomers of this kind, also called macromers, are often designated by a code of the form xxKZn. "xxK" represents the molecular weight of the backbone polymer, which is polyethylene glycol unless otherwise stated, in thousands of daltons. Z designates the biodegradable linkage, where L is for lactic acid, G is for glycolic acid, C is for caprolactone, and TMC is for trimethylenecarbonate. N is the average number of degradable groups in the block. The molecules are terminated with acrylic acid groups, unless otherwise stated; this is sometimes also indicated by the suffix A2.

CROSSLINKABLE GROUPS

The monomers or macromers preferably include crosslinkable groups which are capable of forming covalent bonds with other compounds while in aqueous solution. These crosslinkable groups permit crosslinking of the macromers to form a gel, either after, or independently from thermally dependent gelation of the macromer. Chemically or ionically crosslinkable groups known in the art may be provided in the macromers. The crosslinkable groups in one preferred embodiment are polymerizable by photoinitiation by free radical generation, most preferably in the visible or long wavelength ultraviolet radiation. The preferred crosslinkable groups are unsaturated groups including vinyl groups, allyl groups, cinnamates, acrylates, diacrylates, oligoacrylates, methacrylates, dimethacrylates, oligomethoacrylates, or other biologically acceptable photopolymerizable groups.

Other polymerization chemistries which may be used include, for example, reaction of amines or alcohols with isocyanate or isothiocyanate, or of amines or thiols with aldehydes, epoxides, oxiranes, or cyclic imines; where either the amine or thiol, or the other reactant, or both, may be covalently attached to a macromer. Mixtures of covalent polymerization systems are also contemplated. Sulfonic acid or carboxylic acid groups may be used.

Preferably, at least a portion of the macromers will be crosslinkers, i.e., will have more than one crosslinkable reactive group, to permit formation of a coherent hydrogel by ensuring the crosslinking of the polymerized macromers. Up to 100% of the macromers may have more than one reactive group. Typically, in a synthesis, the percentage will be on the order of 50 to 95%, for example, 60 to 80%. The percentage may be reduced by addition of co-monomers containing only one active group. A lower limit for crosslinker concentration will depend on the properties of the particular macromer and the total macromer concentration, but will be at least about 3% of the total molar concentration of reactive groups. More preferably, the crosslinker concentration will be at least 10%, with higher concentrations, such as 30% to 90%, being optimal for maximum retardation of diffusion of many drugs. Optionally, at least part of the crosslinking function may be provided by a low-molecular weight crosslinker. When the drug to be delivered is a macromolecule, higher ranges of polyvalent macromers (i.e., having more than one reactive group) are preferred. If the gel is to be biodegradable, as is preferred in most applications, then the crosslinking reactive groups should be separated from each other by biodegradable links. Any linkage known to be biodegradable under in vivo conditions may be suitable, such as a degradable polymer block. The use of ethylenically unsaturated groups, crosslinked by free radical polymerization with chemical and/or photoactive initiators, is preferred as the crosslinkable group.

The macromer may also include an ionically charged moiety covalently attached to a macromer, which optionally permits gelation or ionic crosslinking of the macromer.

HYDROPHILIC REGIONS

Water soluble hydrophilic oligomers available in the art may be incorporated into the biodegradable macromers. The hydrophilic region can be for example, polymer blocks of poly(ethylene glycol), poly(ethylene oxide), poly(vinyl alcohol), poly(vinylpyrrolidone), poly(ethyloxazoline), or polysaccharides or carbohydrates such as hyaluronic acid, dextran, heparan sulfate, chondritin sulfate, heparin, or alginate, or proteins such as gelatin, collagen, albumin, ovalbumin, or polyamino acids.

BIODEGRADABLE REGIONS

Biodegradable molecules or polymers thereof available in the art may be incorporated into the macromers. The biodegradable region is preferably hydrolysable under in vivo conditions. In some embodiments, the different properties, such as biodegradability and hydrophobicity or hydrophilicity, may be present within the same region of the macromer.

Useful hydrolysable groups include polymers and oligomers of glycolide, lactide, epsilon-caprolactone, other hydroxy acids, and other biologically degradable polymers that yield materials that are non-toxic or present as normal metabolites in the body. Preferred poly(alpha-hydroxy acids) are poly(glycolic acid), poly(DL-lactic acid) and poly(L-lactic acid). Other useful materials include poly (amino acids), polycarbonates, poly(anhydrides), poly (orthoesters), poly(phosphazines) and poly(phosphoesters). Polylactones such as poly(epsilon-caprolactone), poly(delta-caprolactone), poly(delta-valerolactone) and poly(gamma-butyrolactone), for example, are also useful. The biodegradable regions may have a degree of polymerization ranging from one up to values that would yield a product that was not substantially water soluble. Thus, monomeric, dimeric, trimeric, oligomeric, and polymeric regions may be used.

Biodegradable regions can be constructed from polymers or monomers using linkages susceptible to biodegradation, such as ester, peptide, anhydride, orthoester, phosphazine and phosphoester bonds. The time required for a polymer to degrade can be tailored by selecting appropriate monomers. Differences in crystallinity also alter degradation rates. For relatively crystalline or hydrophobic polymers, actual mass loss may only begin when the oligomeric fragments are small enough to be water soluble. Thus, initial polymer molecular weight and structure will influence the degradation rate.

INITIATORS

The term "initiator" is used herein in a broad sense, in that it is a composition which under appropriate conditions will result in the polymerization of a monomer. Materials for initiation may be photoinitiators, chemical initiators, thermal initiators, photosensitizers, co-catalysts, chain transfer agents, and radical transfer agents. All initiators known in the art are potentially suitable for the practice of the priming technique. The critical property of an initiator is that the polymerization will not proceed at a useful rate without the presence of the initiator.

The "priming" initiator must adhere sufficiently to the surface to be coated to provide a local source of initiation of the reaction with the particular monomers to be applied. The initiator must also not be toxic when used in biologically-related applications, at least in the amounts applied. The initiator is preferably a photoinitiator. In discussing photoinitiators, a distinction may be drawn between photosensitizers and photoinitiators—the former absorb radiation efficiently, but do not initiate polymerization well unless the excitation is transferred to an effective initiator or carrier. Photoinitiators as referred to herein include both photosensitizers and photoinitiators, unless otherwise noted.

Photoinitiators provide important curing mechanisms for addition polymerization, and especially for curing of ethylenically-unsaturated compounds, such as vinylic and acrylic-based monomers. Any of the photoinitiators found in the art may be suitable, if they adhere to the particular surface. Examples of photo-oxidizable and photo-reducible dyes that may be used to initiate polymerization include acridine dyes, for example, acriblarine; thiazine dyes, for example, thionine; xanthine dyes, for example, rose Bengal; and phenazine dyes, for example, methylene blue. Other initiators include camphorquinones and acetophenone derivatives. Photoinitiation is a preferred method of polymerizing the coatings and adhesives.

The choice of the photoinitiator is largely dependent on the photopolymerizable regions. For example, when the macromer includes at least one carbon-carbon double bond, light absorption by the dye causes the dye to assume a triplet state, the triplet state subsequently reacting with the amine to form a free radical which initiates polymerization. In an alternative mechanism, the initiator splits into radical-bearing fragments which initiate the reaction. Preferred dyes for use with these materials include eosin dye and initiators such as 2,2-dimethyl-2-phenylacetophenone, 2-methoxy-2-phenylacetophenone, Darocur™ 2959, Irgacure™ 651 and camphorquinone. Using such initiators, copolymers may be polymerized in situ by long wavelength ultraviolet light or by light of about 514 nm, for example.

A preferred photoinitiator for biological use is Eosin Y, which absorbs strongly to most tissue and is an efficient photoinitiator.

It is known in the art of photopolymerization to use a wavelength of light which is appropriate for the activation of a particular initiator. Light sources of particular wavelengths or bands are well-known.

Thermal polymerization initiator systems may also be used. Systems that are unstable at 37° C. and initiate free radical polymerization at physiological temperatures include, for example, potassium persulfate, with or without tetramethyl ethylenediamine; benzoyl peroxide, with or without triethanolamine; and ammonium persulfate with sodium bisulfite. Other peroxygen compounds include t-butyl peroxide, hydrogen peroxide and cumene peroxide. As described below, it is possible to markedly accelerate the rate of a redox polymerization by including metal ions in the solution, especially transition metal ions such as the ferrous ion. It is further shown below, that a catalysed redox reaction can be prepared so that the redox-catalysed polymerization is very slow, but can be speeded up dramatically by stimulation of a photoinitiator present in the solution.

A further class of initiators is provided by compounds sensitive to water, which form radicals in its presence. An example of such a material is tri-n-butyl borane, the use of which is described below.

REDOX INITIATORS

Metal ions can be either an oxidizer or a reductant in systems including redox initiators. For example, in some examples below, ferrous ion is used in combination with a peroxide to initiate polymerization, or as parts of a polymerization system. In this case the ferrous ion is serving as reductant. Other systems are known in which a metal ion acts as oxidant. For example, the ceric ion (4+ valence state of cerium) can interact with various organic groups, including carboxylic acids and urethanes, to remove an electron to the metal ion, and leaving an initiating radical behind on the organic group. Here the metal ion acts as an oxidizer. Potentially suitable metal ions for either role are any of the transition metal ions, lanthanides and actinides, which have at least two readily accessible oxidation states. Preferred metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous.

CO-INITIATORS AND COMONOMERS

Any of the compounds typically used in the art as radical generators or co-initiators in photoinitiation may be used. These include co-catalysts or co-initiators such as amines, for example, triethanolamine, as well as other trialkyl amines and trialkylol amines; sulfur compounds; heterocycles, for example, imidazole; enolates; organometallics; and other compounds, such as N-phenyl glycine.

Co-monomers can also be used. They are especially useful when the monomer is a macromolecule, as in Example 1 below; in that case, any of the smaller acrylate, vinyl or allyl compounds can be used. Comonomers can also act as accelerators of the reaction, by their greater mobility, or by stabilizing radicals. Of particular interest are N-vinyl compounds, including N-vinyl pyrrolidone, N-vinyl acetamide, N-vinyl imidazole, N-vinyl caprolactam, and N-vinyl formamide.

SURFACTANTS, STABILIZER, AND PLASTICIZERS

Other compounds can be added to the initiator and/or monomer solutions. Surfactants may be included to stabilize any of the materials, either during storage or in a form reconstituted for application. Similarly, stabilizers which prevent premature polymerization may be included; typically, these are quinones, hydroquinones, or hindered phenols. Plasticizers may be included to control the mechanical properties of the final coatings. These are also well-known in the art, and include small molecules such as glycols and glycerol, and macromolecules such as polyethylene glycol.

SURFACES TO BE TREATED

Surfaces to be coated include biologically-related surfaces of all kinds, and include the surface of drug delivery devices such as catheters or prosthetic implants. Any tissue or cell surface is contemplated, as well as the surface of a device to be used in the body or in contact with bodily fluids. A coating may be applied to the surface of any of these, in an amount effective to improve tenacity of adherence. Moreover, the technique may be used to adhere surfaces to each other. For example, wounds in living tissue may be bonded or scaled using this technique or preformed medical appliances may be bonded to tissue. Examples of such applications are grafts, such as vascular grafts; implants, such as heart valves, pacemakers, artificial corneas, and bone reinforcements; supporting materials, such as meshes used to seal or reconstruct openings; and other tissue-non-tissue interfaces. A particularly important class of tissue surfaces is those which are friable, and therefore will not support sutures well. Adherent coatings can seal the suture lines, support sutured areas against mechanical stress, or substitute entirely for sutures when mechanical stress is low. Examples of such situations include vascular anastomosis, nerve repair, repair of the cornea or the cochlea, and repair of the lung, liver, kidney and spleen.

The priming technique can also be used on non-tissue surfaces in general, where useful bonds may be formed between similar or dissimilar substances, and solid or gel coatings are tightly adhered to surfaces. In particular, a pre-formed gel, or other fragile material, may be tightly adhered to a supporting material by this method.

The priming method is advantageous because it can be used to coat and or to bond together any of a wide variety of surfaces. These include all surfaces of the living body, and surfaces of medical devices, implants, wound dressings and other body-contacting atrificial or natural surfaces. These include, but are not limited to, at least one surface selected from the following: a surface of the respiratory tract, the meninges, the synovial spaces of the body, the peritoneum, the pericardium, the synovia of the tendons and joints, the renal capsule and other serosae, the dermis and epidermis, the site of an anastomosis, a suture, a staple, a puncture, an incision, a laceration, or an apposition of tissue, a ureter or urethra, a bowel, the esophagus , the patella, a tendon or ligament, bone or cartilage, the stomach, the bile duct, the bladder, arteries and veins; and devices such as percutaneous catheters (e.g. central venous catheters), percutaneous cannulae (e.g. for ventricular assist devices), urinary catheters, percutaneous electrical wires, ostomy appliances, electrodes (surface and implanted), and implants including pacemakers, defibrillators. and tissue augmentations.

BIOLOGICALLY ACTIVE AGENTS

Biologically active materials may be included in any of the coatings described herein, as ancillaries to a medical treatment (for example, antibiotics) or as the primary objective of a treatment (for example, a gene to be locally delivered). A variety of biologically active materials may be included, including passively-functioning materials such as hyaluronic acid, as well as active agents such as growth hormones. All of the common chemical classes of such agents are included: proteins (including enzymes, growth factors, hormones and antibodies) peptides, organic synthetic molecules, inorganic compounds, natural extracts, nucleic acids (including genes, antisense nucleotides, ribozymes and triplex forming agents), lipids and steroids, carbohydrates (including heparin), glycoproteins, and combinations thereof.

The agents to be incorporated can have a variety of biological activities, such as vasoactive agents, neuroactive agents, hormones, anticoagulants, immunomodulating agents, cytotoxic agents, antibiotics, antivirals, or may have specific binding properties such as antisense nucleic acids, antigens, antibodies, antibody fragments or a receptor. Proteins including antibodies or antigens can also be delivered. Proteins are defined as consisting of 100 amino acid residues or more; peptides are less than 100 amino acid residues. Unless otherwise stated, the term protein refers to both proteins and peptides. Examples include insulin and other hormones.

Specific materials include antibiotics, antivirals, antiinflammatories, both steroidal and non-steroidal, antineoplastics, anti-spasmodics including channel blockers, modulators of cell-extracellular matrix interactions including cell growth inhibitors and anti-adhesion molecules, enzymes and enzyme inhibitors, anticoagulants and/or antithrombotic agents, growth factors, DNA, RNA, inhibitors of DNA, RNA or protein synthesis, compounds modulating cell migration, proliferation and/or growth, vasodilating agents, and other drugs commonly used for the treatment of injury to tissue. Specific examples of these compounds include angiotensin converting enzyme inhibitors, prostacyclin, heparin, salicylates, nitrates, calcium channel blocking drugs, streptokinase, urokinase, tissue plasminogen activator (TPA) and anisoylated plasminogen activator (TPA) and anisoylated plasminogen-streptokinase activator complex (APSAC), colchicine and alkylating agents, and aptomers. Specific examples of modulators of cell interactions include interleukins, platelet derived growth factor, acidic and basic fibroblast growth factor (FGF), transformation growth factor $\beta$ (TGF $\beta$), epidermal growth factor (EGF), insulin-like growth factor, and antibodies thereto. Specific examples of nucleic acids include genes and cDNAs encoding proteins, expression vectors, antisense and other oligonucleotides such as ribozymes which can be used to regulate or prevent gene expression. Specific examples of other bioactive agents include modified extracellular matrix components or their receptors, and lipid and cholesterol sequestrants.

Examples of proteins further include cytokines such as interferons and interleukins, poetins, and colony-stimulating factors. Carbohydrates include Sialyl Lewis$^x$ which has been shown to bind to receptors for selecting to inhibit inflammation. A "Deliverable growth factor equivalent" (abbreviated DGFE), a growth factor for a cell or tissue, may be used, which is broadly construed as including growth factors, cytokines, interferons, interleukins, proteins, colony-stimulating factors, gibberellins, auxins, and vitamins; further including peptide fragments or other active fragments of the above; and further including vectors, i.e., nucleic acid constructs capable of synthesizing such factors in the target cells, whether by transformation or transient expression; and further including effectors which stimulate or depress the synthesis of such factors in the tissue, including natural signal molecules, antisense and triplex nucleic acids, and the like. Exemplary DGFE's are vascular endothelial growth factor (VEGF), endothelial cell growth factor (ECGF), basic fibroblast growth factor (bFGF), bone morphogenetic protein (BMP), and platelet derived growth factor (PDGF), and DNA's encoding for them. Exemplary clot dissolving agents are tissue plasminogen activator, streptokinase, urokinase and heparin.

Drugs having antioxidant activity (i.e., destroying or preventing formation of active oxygen) may be used, which are useful, for example, in the prevention of adhesions. Examples include superoxide dismutase, or other protein drugs include catalases, peroxidases and general oxidases or oxidative enzymes such as cytochrome P450, glutathione peroxidase, and other native or denatured hemoproteins.

Mammalian stress response proteins or heat shock proteins, such as heat shock protein 70 (hsp 70) and hsp 90, or those stimuli which act to inhibit or reduce stress response proteins or heat shock protein expression, for example, flavonoids, also may be used.

The macromers may be provided in pharmaceutical acceptable carriers known to those skilled in the art, such as saline or phosphate buffered saline. For example, suitable carriers for parenteral adminstration may be used.

Methods of Treatment

Generally, any medical condition which requires a coating or sealing layer may be treated by the methods described herein to produce a coating with better adherence. For example, lung tissue may be sealed against air leakage after surgery using the priming technique. Likewise, wounds may be closed; leakage of blood, serum, urine, cerebrospinal fluid, air, mucus, tears, bowel contents or other bodily fluids may be stopped or minimized; barriers may be applied to prevent post surgical adhesions, including those of the pelvis and abdomen, pericardium, spinal cord and dura, tendon and tendon sheath. The technique may also be useful for treating exposed skin, in the repair or healing of incisions, abrasions, burns, inflammation, and other conditions requiring application of a coating to the outer surfaces of the body. The technique is also useful for applying coatings to other body surfaces, such as the interior or exterior of hollow organs, including blood vessels. In particlular, restenosis of blood vessels or other passages can be treated. The techniques can also be used for attaching cell-containing matrices, or cells, to tissues, such as meniscus or cartilage.

GENERAL SEALING OF BIOLOGICAL TISSUES

As shown in the examples below, the priming method of polymerization is especially effective in the sealing of biological tissues to prevent leakage. However, the examples also demonstrate that a degree of sealing can be achieved with photopolymerizable systems without the improvement of priming the tissue with photopolymerizing initiator. There have been numerous attempts to reliably seal tissue with a number of materials, including most prominently cyanoacrylates and fibrin glues. None of these prior art techniques has been entirely satisfactory. Cyanoacrylates, which polymerize on exposure to moisture, and can be accelerated by amines, are very "stiff" once polymerized. If there is any motion of the biological material, they tend to crack, and lose their self-cohesion and/or their adherence to tissue. Fibrin glues can be difficult to prepare, especially in the currently-preferred autologous version; they require enzymatic or toxic chemical means to be gelled or crosslinked; and they are rapidly degraded by native enzymes.

The range of uses of sealing or bonding materials in the body is very large, and encompasses many millions of potential uses each year. In cardiovascular surgery, uses for tissue sealants include bleeding from a vascular suture line; support of vascular graft attachment; enhancing preclotting of porous vascular grafts; stanching of diffuse nonspecific bleeding; anastomoses of cardiac arteries, especially in bypass surgery; support of heart valve replacement; sealing of patches to correct septal defects; bleeding after sternotomy; and arterial plugging. Collectively, these procedures are performed at a rate of 1 to 2 million annually.

In other thoracic surgery, uses include sealing of bronchopleural fistulas, reduction of mediastinal bleeding, sealing of esophageal anastomoses, and sealing of pulmonary staple or suture lines. In neurosurgery, uses include dural repairs, microvascular surgery, and peripheral nerve repair.

In general surgery, uses include bowel anastomoses, liver resection, biliary duct repair, pancreatic surgery, lymph node resection, reduction of seroma and hematoma formation, endoscopy-induced bleeding, plugging or sealing of trocar incisions, and repair in general trauma, especially in emergency procedures.

In plastic surgery, uses include skin grafts, burns, debridement of eschars, and blepharoplasties (eyelid repair). in otorhinolaryngology (ENT), uses include nasal packing, ossicular chain reconstruction, vocal cord reconstruction and nasal repair. In opthalmology, uses include corneal laceration or ulceration, and retinal detachment. In orthopedic surgery, uses include tendon repair, bond repair, including filling of defects, and meniscus repairs. In gynecology/obstetrics, uses include treatment of myotomies, repair following adhesiolysis, and prevention of adhesions. In urology, sealing and repair of damaged ducts, and treatment after partial nephrectomy are potential uses. Sealing can also be of use in stopping diffuse bleeding in any of a variety of situations, including especially treatment of hemophiliacs. In dental surgery, uses include treatment of periodontal disease and repair after tooth extraction. Repair of incisions made for laparoscopy or other endoscopic procedures, and of other openings made for surgical purposes, are other uses. Additional uses include separation of tissues to prevent damage by rugging during healing. Similar uses can be made in veterinary procedures. In each case, appropriate biologically active components may be included in the sealing or bonding materials.

APPLICATION TECHNIQUES AND DEVICES

Both priming and polymer addition may be accomplished by simple dripping of material onto the surface to be coated. This can be accomplished using common devices such as a syringe, a pipet, or a hose, depending on scale. More uniform applications may be obtained using an applicator, such as a brush, a pad, a sponge, a cloth, or a spreading device such as a finger, a coating blade, a balloon, or a skimming device. These may further be used to rub the surface to improve penetration of the primer or the monomer, or to mix primer and monomer in situ on the surface. In large-scale applications, fluid layers may be applied with large-scale coating machinery, including roll coaters, curtain coaters, gravure and reverse gravure devices, and any of the coating devices known in the art. Sprayers may be used at any scale, especially for lower-viscosity primers or polymerizable monomer layers.

Application techniques and devices may be combined, as in applying fluid from a syringe, and then rubbing it into the surface with a finger tip. Such operations may be repeated, as in applying drops of priming initiator; rubbing these into the surface with a brush; repeating this operation; adding monomer solution; rubbing it in; and finally applying additional layers of monomer before or during the application of curing means, such as light, heat, or slow release of peroxide radicals.

An additional application means which is required in many coating techniques described herein, and in particular in the preferred coating method which uses photoinitiation to cure the monomer, is a light source. For large-scale application, flood lamps and similar devices are useful. In small, localized applications, such as tissue sealing and coating, it may be preferable to use a localized source such as a fiber optic or light guide, which can project radiation of the appropriate wavelength onto the site to be treated to cause polymerization of the monomer. Also, a light emitter could be carried on a device, as a miniature bulb. A focused beam from a remote source could be suitable if, for example, the surface was exposed. In exposed surfaces, it is possible that ambient light could he sufficient to polymerize the coating, especially at high initiator levels.

Each of the applications means can be separate, so that a kit of application means could contain, for example, one or more containers or reservoirs, one or more pads or brushes, and if required at least one light guide. The application means could also be combined in whole or in part. For example, a dripping device, such as a tube, could be combined with a spreading device, such as a brush. These could further be combined with a light guide. Such combination devices are especially desirable in treatment of living organisms, and especially humans, to maximize the simplicity of a procedure and the probability of correctly conducting it.

COMPLIANCE PROPERTIES

The compliance properties of the material herein described are those of the material after it has polymerized to form a polymerized material. As used herein, "polymerized material" includes material which forms by the ionic or covalent reaction of monomer precurser molecules. Preferably, the polymerized material is formed by covalent reactions of the monomers. It can be very difficult to measure the elastic properties of the material when adhered to tissue. The mechanical properties are therefore when appropriate measured on samples made in vitro, either in a mold, or, as in the lap-shear test, in contact with standardized tissue. Such measurements must be corrected to conditions applicable to tissue treatment, including the diluting effects of polymerization reagents, or of fluids on the tissue. Thus, a sealing solution may be applied to tissue at a concentration of 30%, but in the coating process it may be diluted to 15% effective concentration by dilution with blood or plasma. Similarly, especially in the case of fibrin sealant, the polymer concentration may be reduced by mixing with polymerizing reagents, either in bulk or by spraying. Where appropriate, such corrections have been taken into account in the descriptions herein. Materials may be equilibrated with water before testing either by absorption or syneresis.

In light of these observations, an effective material for forming a compliant coating or sealant preferably has a strain or elongation before fracture substantially similar to or at least as great as the expected strain during normal use of the tissue to which it is applied, and the elongation of the polymerized material is preferably reversible. This is to avoid either detachment from the tissue or fracture, or limitation of the tissue's natural expansion. Preferably, the effective compliant material will have a reversible elongation at least about 150% as great, more preferably at least about 200% as great, and still more preferably at least about 300% as great as the expected strain of the tissue.

The polymerized material thus may be designed and selected for application to different tissue, to have an elongation at rupture which is similar to or greater than the elongation of the tissue in vivo during its function. The elongation at rupture of the polymerized material can be, for example, greater than 100% or 200%, or optionally greater than 300% or 400%. In some embodiments, the elongation at rupture of the polymerized material may be between for example 100% and 700%, depending on the tissue properties. In some applications, an elongation at rupture greater than 700% is useful.

In addition, the compliant material, for example in sealant applications, preferably should have a normalized compliance that is comparable in magnitude to the normalized compliance of the tissue to which it is applied. The material will be operative even when the material's normalized compliance is much greater than the normalized compliance of the tissue.

In cases where minimal modification of the natural expansion and contraction of a tissue is desired, the preferred range of the normalized compliance ratio extends from about 0.05 to about 3, preferably from about 0.1 to about 2.0, and more preferably from about 0.1 to about 1.0. In some cases, for example when the tissue is lung tissue, a value of the elastic modulus of less than about 150 kPa, preferably less than 100 kpa, more preferably less than about 50 kPa, and most preferably less than about 30 kPa is preferred.

To obtain the desired ratio of the normalized compliance of the polymerized material to the normalized compliance of tissue, the overall force required to stretch the sealant layer should be adjusted, since that of the tissue is fixed. The adjustment can be accomplished by any of several known methods, including the alteration of the thickness of the layer of the polymerized material, or the variation of the polymer concentration, or of the polymer crosslink density, or of other properties of the material. The properties of the precursor materials and the reaction conditions may be adjusted to produce desired other properties of the polymerized material, such as sealant or adhesive properties, or controlled degradation and drug release properties.

Where prevention of tissue deformation is desired, for example during a healing period, the parameters of the tissue coating can be adjusted so that the normalized compliance ratio is significantly in excess of 1.

The adherence of the polymerized material to the tissue is important in order to obtain the benefits of proper compliance properties. An adherence of at least about 20 gm/cm$^2$ in a single or double lap shear test is preferable for many applications. Use of priming technology, described elsewhere in this application, is an effective method for obtaining such values. In some applications, such as the use of the polymerized material as a tissue sealant, adherence values of about 30 gm/cm$^2$ are preferred, and values at or above 40 gm/cm$^2$ are more preferred.

In many applications, such as tissue sealing, the viscosity of the precursor materials can be tailored to obtain optimal coatings. Higher viscosities can favor retention of the uncured or unpolymerized sealant at the site of application, and minimize displacement of the sealant by the presence of bodily fluids at the surface. However, higher viscosities make the material more difficult to apply. A suitable range of viscosity, for example, for the sealant portion of a sealing system is in the range of about 200 cP (centipoise) to about 40,000, preferably about 500 to about 5000 cP, and more preferably about 700 to about 1200 cP. For lung, a suitable range of viscosity is about 900 to 1000 cP. The optimal viscosity will depend on the site of application and the nature of the condition which is to be alleviated by the application of the material.

PACKAGING

The materials for making the coating can be packaged in any convenient way, and may form a kit including for example separate containers, alone or together with the application device. The reactive monomers are preferably stored separately from the initiator, unless they are co-lyophilized and stored in the dark, or otherwise maintained unreactive. A convenient way to package the materials is in three vials (or prefilled syringes), one of which contains concentrated initiator for priming, the second of which contains reconstitution fluid, and the third containing dry or lyophilized monomer. Dilute initiator is in the reconstitution fluid; stabilizers are in the monomer vial; and other ingredients may be in either vial, depending on chemical compatibility. If a drug is to be delivered in the coating, it may be in any of the vials, or in a separate container, depending on its stability and storage requirements.

It is also possible, for a more "manual" system, to package some or all of the chemical ingredients in pressurized spray cans for rapid delivery. If the monomer is of low enough viscosity, it can be delivered by this route. A kit might then contain a spray can of initiator; a spray can or dropper bottle of monomer, initiator and other ingredients; and an optional spreading or rubbing device. If the monomer and initiator system are designed to polymerize under the influence of natural or operating room light, possibly with the supplement of a chemical initiator or carrier such as a peroxygen compound, then the technique could be suitable for field hospital or veterinary situations.

The present invention will be further understood by reference to the following non-limiting examples.

EXAMPLE 1

Relative Adhesion of Coating to Primed and Unprimed Surrfaces

Fresh pig lung was primed in one area with a solution of photoinitiator (Eosin Y, 1 mg/mL (1000 ppm) in normal saline) and in another area with normal saline (prior art control). Excess fluid was removed by blotting. About 0.5 mL of monomer solution was applied to each spot. The monomer was polyethylene glycol (35,000 Daltons) terminated with caprolactone (average of 3.3 caprolactone groups per polyethylene glycol molecule) and capped with acrylic acid, essentially as described in Hubbell et al. The monomer solution contained 15% monomer (w/w), 90 mM triethanolamine, 20 ppm (w/w) Eosin Y, and 5 microliters/mL vinylpyrrolidone (v/v). The samples were irradiated with green light until cured (40 sec. at 100 mW/cm$^2$) into a firm, transparent gel. Initial adherence was seen in both primed and control spots, although the primed spots had better overall adherence.

The lung was connected to a pressure-controlled inflation apparatus, and subjected to chronic fatigue for 1 hour of pneumatic inflation pressures at 25 to 30 cm of water, in 6 second cycles. This was designed to simulate the effects of breathing. After the fatigue test, the primed gel spots were still adherent, but the control gel spots could easily be lifted from the lung surface with forceps. Thus, adhesion under chronic stress was better with priming before polymerization.

EXAMPLE 2

Sealing of Wedge Resection of Lung

In lung operations, it is common to make a "wedge resection" to remove diseased areas. A combination stapler/cutter is used to simultaneously cut and staple along one side of the wedge to be removed, and is then used to staple and cut the other side so that a wedge-shaped piece of lung is removed, while the remaining lung is simultaneously stapled closed. Despite a high staple density, the staple lines are prone to leak air, which can produce severe complications in a patient undergoing such an operation.

Frozen-thawed pig lungs were wedge-resectioned, using a ProxiMate™ TLC 55 reloadable linear cutter/stapler (Ethicon; Somerville, N.J.). Every second staple was omitted from the outer staple lines in the cassette to reliably induce leaks. Lungs were inflated with air to a pressure of 40 cm $H_2O$, and leaks were observed by pushing the stapled area just under the surface of a water bath (similar to leak testing of an inner tube). Next, staple lines were primed with 1000 ppm Eosin Y, blotted, and treated with the macromer mixture of Example 1 which was then cured as described.

In a standard test for durability, the lungs were inflated to 20 cm water pressure for 10 cycles, over a period of 1 minute, and then held for 30 seconds at 40 cm water. The primed and sealed lung sections showed no leaks, demonstrating the effectiveness of the priming system in sealing known leaks.

Finally, pressure was increased in the primed lungs to determine the maximum pressure before leakage. Small leaks were typically seen at 75 cm water or above.

EXAMPLE 3

Lap/Shear Strength of Primed and Unprimed Bonds

Adhesion under shear of gel to rat skin was determined on an Instron™ apparatus using standard methods. The biological surface was rat back skin, freshly removed from euthanized animals. It was glued to a glass slide, and treated as described below. A casting chamber was positioned above the skin, which also contained a gauze mesh which protruded from the chamber. Monomer solution was injected into the chamber and polymerized. The chamber was removed, and the tensile strength of the bond was determined by shearing the lap between the glass slide and the gauze mesh in a standard load cell on the Instron™.

Skin treatments included none (control); primed; primed and pre-coated with monomer solution by drip; and primed, pre-coated with monomer solution by drip, and rubbed or mixed with a brush. A monomer solution as in Example 1 was applied, except that the monomer, "8KL5", had a smaller PEG molecule (8000 D), and was extended with lactate groups rather than caprolactone groups. With unprimed skin, a different initiator, Irgacure™ 651 (Ciba Geigy), was also used in the gelling monomer mixture.

With the non-primed Irgacure™ system, average load at failure for 6 to 8 samples ranged from 49 grams of force with low-intensity mixing of monomer onto the surface, to 84 to 274 g. with rubbing. Similar results were obtained with the Eosin catalysed system with no primer (146 g average, range 80–220). When the tissue was pre-primed with Eosin, and monomer solution was thoroughly mixed with a brush, the failure force increased to 325 g (range 220–420). Thus priming can quantitatively improve early adherence, in addition to its much larger improvement in adherence after flexing.

EXAMPLE 4

Sealing of a Bronchus

A bronchus was stapled and cut during lobectomy by the techniques described for wedge resectioning. The staple line was coated as described in Example 2, likewise preventing or stopping air leaks.

EXAMPLE 5

Sealing of a Laceration

A laceration 2 mm deep by 2 cm long was made on an isolated lung with a scalpel; the scalpel was taped to control the depth of cut. The lung was tested and found to leak. The laceration was primed, filled with monomer solution containing initiator, and the monomer was photopolymerized. The leak was sealed by this procedure.

EXAMPLE 6

Coating of a Medical Device

A length of polyurethane tubing extrusion used for catheter shafts was dipped into an aqueous solution containing 20 ppm eosin. Excess eosin was rinsed off with water. The primed tubing was dipped into a solution containing 10% monomer (type 8KL5, as in example 3), 90 mM triethanolamine, 5 ppm vinylpyrrolidone, and 20 ppm eosin. Excess monomer was allowed to drip off. The monomer layer on the tubing was then photopolymerized to form an adherent gel coating. The adherence was strong enough to survive sectioning of the tubing with a razor blade; photomicrography showed complete adherence of the gel to the tubing. As a prior art control, the shaft was not primed. After dipping the un-primed shaft into the same monomer solution, the coating on the shaft was photopolymerized. A gel was formed, but failed to adhere to the shaft, and fell off during handling.

EXAMPLE 7

Priming for Surface Adherence

Two surfaces of Pebax™ polyeteramid were stained with 1000 ppm Eosin Y and rinsed. Polymerizable monomer solution (10% 8KL5 in water containing 20 ppm eosin) was placed between the surfaces, and the sandwich was exposed to green light. Gel formed in the interface and held the surfaces together. In a control experiment, in which the surfaces were not primed, polymerization of the monomer occurred but no significant adherence of the surfaces was found.

EXAMPLE 8

Priming of Surfaces

On exposure to 1000 ppm of Eosin Y, surfaces of Teflon™ fluoropolymer and of polyethylene were observed to stain significantly. When monomer was added to such surfaces, and allowed to stand briefly, gels were formed on illumination. Adherence seemed inferior to that obtained on polyurethane.

EXAMPLE 9

Priming of Uterine Horn and Adherence of Gel Layers

A model system was established for placing of barriers on mammalian uteruses after operations. Freshly excised uterine horns from euthanized pigs were removed from a saline bath and treated with 1000 ppm Eosin. Controls were not primed. Polymerizable monomer solution as in Example 7 was applied to the primed and control areas. Adherence of gel layers to the primed areas was very firm, while gels on control areas could be dislodged.

EXAMPLE 10

Water-Sensitive Initiation

It is known to use tributylborane as a water-sensitive initiator of bulk polymerization. In this example, it is shown that TBB can serve as an initiator in interfacial polymerization, and thus as a primer.

1 M tributylborane (TBB) solution in THF was purchased from Aldrich. Lyophilized 35KL4A2 reactive monomer containing triethanol amine and eosin was made in these laboratories. Polyethylene glycol 400 (PEG 400) was obtained from Union Carbide). Of the lyophilized powder of 35KL4A2, 0.5 gram was dissolved in 9.5 grams of PEG 400. The mixture was warmed using a heat gun up to 40–50° C. to facilitate dissolution. To this solution, 30 µL of vinyl pyrrolidinone were added as a comonomer.

Using a glass syringe, 2 ml TBB solution were transferred to a sprayer, of the type used with thin layer chromatography plates. A small amount of TBB solution was sprayed on a glass coverslip and the PEG 400 solution containing 35KL4A2 was applied on the TBB solution. An immediate polymerization of the solution was noticed. The polymerized film was insoluble in water indicating crosslinking.

Similar polymerization was carried out on pig lung tissue. A small amount of TBB solution was sprayed on approximately 3 cm$^2$ of lung tissue. A 35KL4A2 solution in PEG was applied on top of the TBB solution. A small amount of TBB solution was also sprayed on top of the monomer solution. A well adherent film of 35KL4A2 on lung tissue was noticed. The polymerized film was elastic and well adherent to the tissue.

In an alternative procedure, application of the TBB initiator to tissue may be followed by application of monomer solution containing a photoinitiator, such as 20 ppm eosin. Photopolymerization is then used to build a thick layer of gel onto the initiated priming layer. Good adherence is predicted.

EXAMPLE 11

Combination of Redox Free Radical Initiation Systems with Photoinitiation and/or Thermal Free Radical Initiation Systems for Increased Polymerization Speed Previous visible light photopolymerization of Focal macromonomers uses the aqueous eosin Y/triethanolamine photoinitiation system. This reaction has been observed to generate peroxides when carried out in the presence of dissolved oxygen in the buffer. One may exploit these generated peroxides as an additional source of free radical initiators for polymerization using a Fenton-Haber-Weiss style reaction. In an effort to use these formed peroxides as polymerization initiators, ferrous ion in the form of ferrous sulfate was added to the eosin Y/triethanolamine buffer and used in the photopolymerization of Focal macromonomers. Using an indentation style hardness test, gel stiffness as a function of illumination time was used as a measure of gel cure.

In an experiment to evaluate the effectiveness of 50 ppm ferrous ion on the gelation of the Focal macromonomer 8KL5, two buffers were prepared. The first buffer was prepared in deionized (DI) water using 90.4 mM triethanolamine (TEOA) and pH adjusting to 7.4 with 6 N HCl. The second buffer was prepared similarly but with the addition of ferrous sulfate such that there would be approximately 50 ppm ferrous ion available. These buffers were used to prepare a 10% (w/v) 8KL5 gelling solution with 1 microliter of vinyl pyrrolidinone per ml of gelling solution added as a comonomer. These solutions were then divided into gelling samples and had 20 ppm of eosin Y added to them. These samples were then illuminated using an all lines Ar laser at a power of 100 mW/cm$^2$. All illumination timepoints were done in triplicate and kept dark until stiffness testing was performed. In comparing a 10% (w/v) Focal macromonomer gelling solution with and without 50 ppm of ferrous ion added, the gel with the added iron gave significantly more cured gels than did the gel without iron.

It is further believed that any free radical initiation system, especially aqueous ones, capable of generating soluble peroxides can be greatly enhanced by the addition of soluble metal ions capable of inducing the decomposition of the formed peroxides.

EXAMPLE 12

Redox-Accelerated Curing ("Dual Cure") of Primed Systems

A redox-accelerated system was compared to a purely photoinitiated system for priming tissues. The accelerated system was found to be especially effective in the presence of blood, which attenuates the light used in photopolymerization. An acute rabbit lung model of sealing of air leaks was used. A thoracotomy was made under anesthesia in the intercostal space of the rabbit. Anesthesia was induced using an intramuscular injection of ketamine-acepromazine. The seventh rib was removed to facilitate access to the lungs, and the animal was maintained on assisted ventilation. A laceration, about 8 mm×2 mm, was made on each of the middle and lower lobes of the lung. Air and blood leaks were immediately apparent. Bleeding was tamponaded using a gauze sponge, and the site was then rinsed with saline. Some blood remained, and a slow ooze of blood and air leakage from the site was still persistent on ventilation.

Two formulations were compared. In the first formulation, the priming solution contained 500 ppm Eosin Y and 90 mM TEOA (triethanolamine) in WFI (water for injection), while the macromer solution contained 15% w/v macromer (type 35KL4), 20 ppm Eosin Y, 5 mg/ml vinylcaprolactam, and 90 mM TEOA in WFI.

The second formulation contained 500 ppm Eosin Y, 15% 35KL4, and 3 mg/ml ferrous gluconate in WFI in the primer, and the same macromer solution as in the first formulation, supplemented with 500 ppm t-butyl peroxide.

Application methods were the same for both formulations, and consisted of application of 1 ml primer with gentle brushing, followed by application of 0.5 ml macromer solution by brushing, and then illumination with blue-green light at 100 mW/(square centimeter) while dripping an additional 0.5 ml of macromer. Total illumination time was 40 sec. Gels were formed on the tissue by both treatments, and the air and blood leakages were sealed.

Acute adhesion of the gel to tissue was rated on a scale of 1 (poor) to 4 (excellent). The first formulation scored 1.5, and the second scored 3.5. A notable improvement in adherence of the gel to the living lungs was seen with the use of the dual cure system.

EXAMPLE 13

Optimization of Iron Concentrations

The objective is to find a redox system which does not instantaneously gel the macromer, and which can also be cured by light. Various formulae were prepared, and their polymerization was studied.

A stock monomer solution (solution 1) contained 15% w/w "35KL4" macromer, lot 031395AL, in TEOA buffer (90 mM triethanolamine, neutralized to pH 7.4 with HCl, in water for injection), and 4000 ppm VC (vinylcaprolactam) and 20 ppm eosin Y (photoinitiator). The buffer was selected to be compatible with dissolved iron.

Iron-monomer solution (solution 2) contained in addition 20 mg/ml of ferrous gluconate, 5.8 mg/ml of fructose, and 18 mg/ml of sodium gluconate.

Peroxide primer (solution 3) contained: 500 ppm eosin in TEOA buffer, plus 5 microliter/ml of 10% tertiary butyl peroxide. An alternative priming solution (3b) contained in addition 10% 35KL4.

Serial dilutions of one volume of iron monomer with two volumes of stock monomer were made, and the gelation time, in the absence of high-intensity light, upon addition of 1 volume of priming solution (3) to two volumes of diluted iron monomer was determined. The stock iron monomer and the 1:3 dilution gelled very rapidly (1–2 seconds), and a 1:6 dilution gelled in 3–4 seconds. The 1:9 dilution gelled very slowly no rapid gelation, and partial gelation after 1 hour. Further dilutions (1:27, 1.81) did not gel for at least one hour.

The formulation with 1:9 dilution, containing about 2.2 mg/ml of ferrous gluconate, was tested for its ability to adhere to excised tissue, and to gel in the presence of blood. Acute adherence was obtained with 1:9 iron monomer solution when primed with the basic peroxide priming solution, but better adherence was found with monomer-containing priming solution (3b).

In solution, a mixture of monomer solution (0.3 ml) and normal primer (0.13 ml; without peroxide), which polymerized when exposed to intense argon laser light, would not gel after addition of 2 drops of blood (about 33 mg). However, a mixture of the same volumes of 1:9 iron monomer, primer 3b, and blood gelled in 5 seconds on exposure to the same light source. Omission of the Na gluconate and fructose did not significantly change the gel time. The mixed formulation (iron monomer, peroxide primer, and blood) could be held for three hours in amber glass at room temperature with only slight decrease in the gelling time on exposure to light.

Thus, the formulation is sufficiently stable and controllable under operating room conditions, so that a preparation could be reconstituted at the start of the operation, and the material would be useful and applicable to tissue throughout the operation.

EXAMPLE 14

Adherence to Tissue at Varied Concentrations of Peroxide and Iron

Areas of excised fresh or frozen-thawed pig lung were primed with a photoinitiator, and a gel formed on the spot by dripping of photoinitiator-containing monomer. In contrast to the previous example, the iron (ferrous gluconate) was in the primer, and the peroxide in the monomer solution. Gels formed by illumination at peroxide concentrations ranging from 76 to 900 ppm, and iron concentrations ranging from 1500 to 5000 ppm, had at least moderate adherence to tissue after overnight incubations.

EXAMPLE 15

Redox Interfacial Primed System

It was demonstrated that non-photopolymerization techniques can produce gels adherent to tissue. Thinly-sliced ham was soaked in deionized water, and a 1 by 2 inch piece was folded in half and the outer edges were bonded together. First, 0.1 ml of solution A was applied to the joint (Solution A contained 10% monomer 8KL5, 0.3% hydrogen peroxide, and 0.3% NVMA (N-vinyl N-methyl acetamide)). Then 0.2 ml of Solution B was applied. (Solution B contained 30% 8KL5, 20 mg/ml Ferrous Ammonium Sulfate hexahydrate (Aldrich), 3% fructose, and 0.3% NVMA. Cure was instantaneous, and no discoloration of the gel occurred. The bond held during overnight soaking in distilled water.

EXAMPLE 16

Sprayed Redox System

Using the above solutions, and with monomer concentrations varying from 5% to 10% in solution A and 10% to 30% in solution B, primer (solution A) was sprayed on semivertical surfaces, followed by solution B. Surfaces were the palm of the experimenter's hand, and petri dishes. The spraying procedure caused some foaming, but gels were formed on all surfaces. Because of running of the solutions down the surfaces, gels were thicker at the bottom but present throughout. In a similar experiment, the monomer 8KTMC, containing trimethylenecarbonate biodegradable linkages between the polyethylene glycol and the acrylate cap, seemed to adhere somewhat better than the 8KL5.

EXAMPLE 17

Comparison of Peroxygen Compounds

Reductant solutions contained 10% 8KL5 monomer and 8% by volume of a ferrous lactate solution, which itself contained 1% ferrous lactate and 12% fructose by weight in water. Oxidant solutions contained 10% 8KL5 monomer and a constant molar ratio of oxidizer, which was, per ml of macromer solution, 10 microliters 30% hydrogen peroxide; 8.8 microliters tert-butyl peroxide; 15.2 microliters cumene peroxide; or 0.02 g potassium persulfate. 0.5 ml of reductant was mixed with 0.25 ml oxidizer, and time to gelation was noted. With hydrogen peroxide, gelling was nearly instantaneous, while with the others there was a short delay—about 1 second—before gelation. Doubling the t-butyl peroxide concentration also produced nearly instantaneous gelling. Hydrogen peroxide produced more bubbles in the gel than the others; persulfate had almost no bubbles. The bubbles in hydrogen peroxide may come directly from the reactant, as the other compounds have different detailed mechanisms of radical formation.

EXAMPLE 18

Effect of Reducing Sugars

Using the procedures of Example 17, the concentration of ferrous ion was reduced to 50 ppm, and the fructose was omitted. At 100 ppm HOOH in the oxidizing solution, gel time was increased to 3 to 4 seconds, with both Fe-gluconate and Fe-lactate, but gels were yellow. Addition of 125 ppm ascorbic acid to the reducing solution prevented the formation of the yellow color.

EXAMPLE 19

Sodium Gluconate Addition

It was found that raising the pH of the iron-peroxide system from 3.7 to 5.7 by addition of sodium gluconate had no effect on gelation time.

EXAMPLE 20

Compatibility with Ultraviolet Photoinitiators

Solution A contained 1 g 8KL5, 0.4 ml of a ferrous lactate solution (containing 0.4 g ferrous lactate and 4.8 g of fructose in a final volume of 40 ml of distilled water), and 8.6 g of distilled water. Solution B contained 1 g of 8KL5, 0.1 ml of 30% hydrogen peroxide, and 8.9 g water. Drops of A were allowed to fall into a solution of B, resulting in drops of gel which gradually accumulated at the bottom of the solution. If solution B was supplemented with 4% by volume of a solution of 0.2 g of Irgacure™ 651 photoinitiator dissolved (with heating) in 4 ml of Tween™ 20 detergent, then after making bead droplets as before, the entire solution could be gelled by application of UV light. This demonstrates the compatibility of the redox and UV-curing systems. Moreover, it would be possible to make the redox-cured droplets from a monomer which would degrade either faster or slower than the continuous-phase gel, as desired, thereby potentially creating a macroporous gelled composite.

EXAMPLE 21

Relative Adherence of Gels

Various gel formulas were compared in their ability to stick to domestic ham, versus their ability to adhere the fingers of the hand together. It was found that adherence of a formula to one type of surface was only weakly predictive, at best, of the adherence to the other. In another experiment, it was found that persulfate-catalysed gels are less adherent to tissue than comparable t-butyl peroxide gels, but are relatively more adherent to metal. Thus, the optimal formulation may well depend on what is to be coated with gel.

EXAMPLE 22

Intra-Pleural Sealing

A source of morbidity in lungs is the formation of bullae, which are sacs formed by separation of the plerua from the lung parenchyma. As a model for possible repair of bullae, the pleura of a detached lung was repeatedly nicked to generate small air leaks. Then a solution containing 15% of 35KL18 macromer, 20 ppm of eosin, 5 milligrams/ml vinylcaprolactam, and 90 mM triethanolamine was injected between the pleura and parenchyma at the sites of the air leaks. The solution spread preferentially between the tissue layers, forming a blister-like structure. The area was transilluminated from the pleural side with blue-green light for 40 seconds. A flexible gel was obtained, and the air leaks were sealed.

A similar procedure could be applied to other layered tissues to stop leaks and effusion. Because the gel is confined within the tissue, adherence to tissue is not a primary concern. There are a number of anatomical structures having layered tissue structurees suitable for this method of sealing a tissue against leakage. Such tissue layers include the meninges, including the dura, the pia mater and the arachnoid layer; the synovial spaces of the body including the visceral and pareital pleurae, the peritoneum, the pericardium, the synovia of the tendons and joints including the bursae, the renal capsule, and other serosae; and the dermis and epidermis. In each case, a relatively fragile structure can be sealed by injection of a polymerizable fluid between adjacent layers, followed by polymerization. Formation of a biodegradable, biocompatible gel layer by non-intrusive processes such as photopolymerization is especially desirable, because it minimizes trauma to the tissue.

EXAMPLE 23

Sealing of an Injured Artery

In an anesthetized pig, a 1.5 cm lengthwise incision was made in a carotid artery. The incision was closed with interrupted sutures, so that blood seepage occurred. The injured area was rinsed with saline, and the blood was suctioned from the treatment zone. The treatment zone was primed with 1 mg/ml eosin in buffer (TEOA in ⅓ normal phosphate buffered saline). A macromer solution was applied with a small paintbrush to the treatment zone under illumination with blue-gree argon ion laser light. In a first artery, the macromer solution contained 15% 35KC3.3, 4 mg/ml N-vinylcaprolactam, and 20 ppm eosin. In a second artery, the macromer was type 35KL18, and the macromer solution has a paste-like consistency. Four applications (0.5 to 1.0 ml each) were required to seal all leaks. It was easier to build thickness with the paste-like monomer. The pig was held under anesthesia for an hour, and the injury sites were reexamined and found to be still sealed.

EXAMPLE 24

Adherence of Coating Layers to Living Tissue Surfaces

An experiment was performed to evaluate the acute adherence of a formulation of 20% macromer 35KTMC8A2. with redox/eosin primer to uninjured tissue in situ. An immature pig (est. 35 kg) was maintained in an anesthetized condition and various tissues and prosthetic implants (described below) were surgically exposed or prepared. Care was taken to prevent injury to the tissues; however, the dissection of connective tissue often resulted in a roughened surface where the primer/polymer was applied.

The primer and macromer were applied with separate paint brushes, and light was delivered from a bare 2 mm diameter optical fiber. The light source was periodically checked and consistently emitted approx. 580 mW of visible light through the course of the experiment at the distal tip of the delivery fiber.

The acute adherence was graded on a 1–4 scale, where 3 or better is considered acceptable: "4": cohesive failure into small pieces when the deposited gel is gripped with blunt tweezers and pulled perpendicular and/or parallel to the tissue surface.

"3": cohesive failure with larger fragments.

"2": combined cohesive/adhesive failure.

"1": adhesive failure, gel lifts off in continuous film.

A. Adherence to tissues (Tissue/adherence grade):
1) Lower stomach (proximal to pylorus)—3.5 The stomach was reexamined after 1 hour indwelling—<3.5. Still adherent, but less than at time=0. Tear strength deteriorated.
2) Common bile duct—3.5.
3) Urinary bladder 3.8 (Punctate bleeding was noted on the bladder; it was confirmed hat the causes were brushes and manipulation).
4) Ureter—3.5–3.8;
5) Large bowel (descending colon 8 cm anterior to pubic bone)—4.0
6) Esophagus—3.5.
7) Patellar tendon (2 cm proximal to tibial attachment)—3.5
8) Cartilage (trochlea groove of knee)—2.5 This tissue didn't stain with eosin; polymerized gel peeled off in sheets. Removal of upper hyaline layer, deep enough for minor blood oozing to appear, improved score to 2.8.

B. Adherence to other implantable materials.:
9) Collagen coated Dacron patch—3 This was a Datascope woven Dacron graft material 8 mm diameter. Collagen impregnated; 6-0 Prolene sutures.
10) Abdominal aortic graft—3.5. This was a Meadox Dacron double velour (inside/outside); 6 mm Inside diameter; Cat No. 174406. Lot No 245246. Sterilized 1986. The graft was preclotted in autologous blood. The animal was heparinized before implantation.

11) Gore FEP (fluorinated ethylene propylene) in vitro test—0. Material would not stain; cured polymer slid off without effort.
12) Carotid Gore patch—2.5–3. Polymer adhered to sutures and surrounding tissue.
13) Hernia mesh—2.5 (more or less). Polymer was used to anchor the mesh (by U.S. Surgical) onto external abdominal oblique fascia. The polymer was suitable for positioning, but did not provide "structural" anchoring.

EXAMPLE 25

Process for Sealing Medical Devices to Body Tissues

There is a need to seal or bond medical device surfaces to tissue. To be successful, this application requires the sealant or adhesive to form strong bonds to both the device and the tissue. Important examples of this application apply to sustained use devices such as percutaneous catheters (e.g. central venous catheters), percutaneous cannulae (e.g. for ventricular assist devices), urinary catheters, percutaneous electrical wires, ostomy appliances, electrodes (surface and implanted) and the like. In such devices, there is a tendency of the implant or device to move relative to the surrounding tissue. Such movement can allow entry of microorganisms, or can intensify the reaction of the tissue to the implant. Moreover, when a device is inserted percutaneously, then during the process of healing the epidermis in contact with the implant may undergo "marsupialization", or the formation of a partial pouch along the surface of the implant. This can retard healing of the percutaneous opening, following removal of the device.

In scope, the process includes sealing the device/tissue interface for any medical device that crosses or disrupts a tissue layer whose continuity provides a natural defense mechanism against infection or bodily fluid loss (skin, mucous membranes). This technology is also applicable to obliterating potential space between implanted devices that do not allow tissue ingrowth/ongrowth and the implant bed, serving to reduce device movement which is a cause of chronic inflammation. These tissue-device sealants may also serve as matrices for drug delivery, for example the delivery of antimicrobials to prevent infection.

Bioabsorbable hydrogels and non-absorbable analogs are appealing for these applications in that they may be formed in place to seal (or "caulk") around the device. Hydrogels usually adhere poorly to hydrophobic device surfaces which comprise most of the examples listed above.

However, a process is provided herein which produces a strong attachment of hydrogel to a hydrophobic surface during in situ polymerization of hydrogel components. It involves applying a primer containing adequate concentrations of an initiator of polymerization (Eosin Y and/or other ingredients) to a hydrophobic surface (in the example below, polystyrene, in a 12 well plate) following with a sealant composition based on a polymerizable macromer (in this example containing triethanolamine co-initiator), and effecting polymerization. The different embodiments, 25.1–25.3, are described below.

25.1: Into one well of a 12 well microtiter dish was placed 0.1 ml of a primer solution containing 500 ppm eosin with ferrous gluconate (5 mg/ml), fructose(10 mg/ml), and macromer 3.3KL5A2 (30%). Then 0.9 ml was added of a solution containing 12.8% of macromer F127T4A2 (i.e., poloxamer Pluronic F127, with 4 units of trimethylene carbonate and acrylate end caps), 125 ppm t-butyl peroxide, 90 mM triethanolamine and 0.4% VC (N-vinylcaprolactam). The mixture partially gelled on mixing, but the gel was not coherent. After illumination with blue light for 2× 20 sec., a coherent gel was formed. However it was not tightly adhered to the surface of the plastic.

25.2: The experiment was repeated, but the eosin concentration was raised to 2000 ppm. Initially the solution did not gel as well, but on illumination the gel adhered strongly to the plastic.

25.3: The experiment was repeated at 2000 ppm eosin concentrations, but without the "redox" components (ferrous gluconate, fructose, t-butyl peroxide). Adherence was stronger at 2000 ppm eosin (alone) than at 500 ppm even with redox materials, although not as strong as with the redox components present.

The results are compatible with the idea that the eosin was absorbing to the surface of the plastic during the course of the experiment. To validate this, a solution containing 12.8% macromer (F127T4A2), the usual VC and buffer, no redox components, and 2000 ppm eosin was applied to a well and allowed to stand for about 10 seconds. The gel was strongly adherent. In a comparable experiment at 100 ppm eosin, the gel was formed but adhered weakly.

Thus, a critical variable here appears to be the level of photoinitiator—here eosin—in the primer. Relatively high concentrations (2000 ppm) gave stronger bonds of hydrogel to polystyrene than lower amounts. The use of "redox" coinitiators gave stronger gels, but high Eosin levels gave strong bonds with or without "redox" coninitiation.

In other experiments, it was demonstrated that the system that gave the strongest bonds to the polystyrene also gave very strong bonds to animal tissue (cadaveric goat gingiva). The strong bonding of sealant to polystyrene 12 well plates may thus used (in the absence of tissue)to demonstrate the tissue bonding capability of a particular hydrogel, thus minimizing experimentation. This system, applied simultaneously to a tissue and a hydrophobic device (via application of primer, sealant, and light) would thus appear to result in an effective tissue-to-device sealant with wide-ranging applicability.

EXAMPLE 26

Use of Redox-Assisted Photoinitiation in Treatment of Injured Arteries

The interior of a rabbit carotid artery was injured by scraping with an inflated balloon catheter. The injured area was then isolated with a two balloon catheter, and the injured zone was flushed with saline; stained on its surface with an initiator solution, containing 20 ppm eosin Y in PBS (phosphate-buffered saline, pH 7.4);further flushed with saline to remove unbound eosin; treated with a buffered solution containing 90 mM TEOA (triethanolamine), pH 7.4; 30% by weight of polymerizable macromer; 0.2% to 0.25% of vinylpyrrolidone or vinylcaprolactam; and optionally 50 ppm of ferrous sulfate. The treatment zone was then exposed to 100 mW/sq. cm. of green light from an argon laser for 20 seconds. The balloons were collapsed and blood flow was permitted to resume, resulting in flushing of excess macromer from the zone into the rest of the circulation. In various tests, it was found that a thin layer of gel was formed on the inside of the artery both with and without the addition of ferrous ion. It was further found that the layer persisted for longer times in the presence of the ferrous ion.

To better understand this system, gels were formed in test cells, and their mechanical properties after various lengths of illumination were compared. It was found that the addition of iron resulted in gels which were better cured and which were relatively less sensitive to the exact concentration of other reagents, or to the duration of illumination. This is shown in more detail in Table 1:

TABLE 1

Ratio of Modulus at 20 sec. to 90 sec. of Illumination

TABLE 1

| Ratio of Modulus at 20 sec. to 90 sec. of illumination | | | |
|---|---|---|---|
| Illumination | Redox conc. | 20 ppm eosin | 100 ppm eosin |
| 100 mW/cm2 | 50 ppm Fe | 93% | 83% |
|  | 0 ppm Fe | 63% | 14% |
| 400 mW/cm2 | 50 ppm Fe | 98% | 77% |

Conditions: 30% 3.3KL5 in 90 mM TEOA pH 7.4 and 2 $\mu$L VP/mL

The ratio of the gel modulus at 20 sec. illumination to 90 seconds is a measure of the rapidity of complete polymerization of the gel. Higher numbers denote faster polymerization. It can be seen that the addition of iron markedly accelerates the cure, and that this effect is more pronounced at 100 ppn eosin, where the underlying variation is greater, and likewise at lower light levels.

EXAMPLE 27

Redox Systems with Urethanes, Acids and Amides, using Ceric Ion

The objective of the experiment was to determine the feasibility of making polar-ionic macromers using a Ce-IV based redox system with urethanes, carboxylates or amides as reductant. A special macromer was made (3.3KL5A1: 3.3K PEG; 5 lactides; 1 acrylate) and end-capped with diisocyanate to form a urethane by standard procedures.

The different embodiments, 27.1–27.4, are described below.

27.1: Add 1 ml of methacrylic acid to 10 ml of 2.25 wt. % Ceric ammonium nitrate in water ("Ce solution"; has yellow color). A white precipitate was formed immediately; the yellow color faded over time.

27.2: Add 10 ml Ce solution to a 10 ml solution containing 0.5 ml acetic acid and 0.5 ml methyl acrylate. A white precipitate formed immediately, and the yellow color gradually faded.

27.3: Add 1 g of the NCO-end capped initiator to 10 ml of Ce solution, and mix with 10 ml of a 50% w/v solution of AMPS (acrylamido methyl propanesulfonic acid). The solution remained yellow and unprecipitated. However, after standing overnight at room temperature the solution had become colorless and highly viscous, and was not filterable through a 0.2 micron filter. This suggests a high degree of polymerization, perhaps with some crosslinking.

27.4: A carboxylate-terminated macromer was made by treating 3.3KL5A1.0 with succinic anhydride. The purified reprecipitated polymer was dissolved in deionized water (0.39 g/7 ml) and 2.0 g of AMPS was added. The pH was adjusted to 3.8 with NaOH. Then 55 mg. of Ce(IV) ammonium nitrate was added (approximately stoichiometric with the expected number of carboxyl groups). The volume was adjusted to 10 ml. with water. The solution rapidly became turbid and increased in viscosity, and appeared to be crosslinked to a gel within about 1 hr. The resulting gel could be dissolved by pH 13 NaOH solution in about 1 hr., showing that the crosslinks involved the degradable ester moieties.

It appeared that both carboxylic groups and urethane groups can serve as reductants for ceric ion in a redox-catalysed polymerization of an unsaturated group. Other groups known to be effective in such reactions can also be used where the conditions are physiologically reasonable.

EXAMPLE 28

Adherence of Medical Device Material to Tissue

In this example, direct adhesion of a typical medical polymer to tissue is demonstrated. It is further shown that the location of the plane of fracture of the composite can be controlled by selection of concentration and type of photo-initiator.

Microscope-slide-sized pieces of Pellethane (Dow) extruded polyurethane sheet were washed with acetone to remove impurities and dried in a vacuum oven. They were then stained with a solution of 2000 ppm Eosin Y in PBS, as above, for several minutes until pink staining of the polyurethane was observed. Sheets were rinsed in water and air dried.

Pieces of abdominal wall were excised from a euthanized rat, and used with the peritoneal side "up" ("tissue"). Tissue was clamped to a glass slide with binder clips. Thin Teflon spacers were placed on top of the tissue. Dried sheets of urethane were clamped into the sandwich, eosin-stained side towards the tissue, forming a thin chamber between the polyurethane and the tissue, typical of clearances found in medical practice. Four combinations of solutions were tested.

The different embodiments, 28.1–28.4 are described below.

28.1: About 0.2 ml of a primer solution containing 2000 ppm eosin in PBS was infused into the chamber, and was removed by wicking after about a minute. A macromer solution (about 0.2 ml) was added, containing 12.8% F127T4A2 macromer (as in example 27), 90 mM TEOA and 0.4% VC (vinyl caprolactone), and, in this experiment, 2000 ppm eosin. The chamber was transilluminated through the glass slide and rat flap for 40 seconds. The macromer did not completely polymerize, and on removal of the clamps the tissue separated from the urethane without appreciable force.

28.2: The above experiment was repeated, but the eosin concentration in the macromer solution was reduced to 20 ppm. Polymerization was complete. On separation of the tissue from the urethane, the gel fractured while remaining adherent to both tissue and to the urethane.

28.3: The above experiment 28.2 was repeated, except that the redox accelerator t-butyl peroxide was present in the macromer solution at 125 ppm, and the primer contained Ferrous gluconate and fructose as in Example 25.1. The gel was completely polymerized. On attempting to peel the tissue from the urethane, the tissue tore—i.e., both the gel and its bonds, to both tissue and device, were stronger than the tissue itself.

28.4: Experiment 28.2 was repeated, except that the concentration of eosin in the primer was reduced to 20 ppm.

Polymerization was complete. On peeling the tissue, failure of adhesion occurred at the interface between the gel and the tissue.

This example demonstrates that by selection of initiator types and concentrations, the fracture plane of a device bonded to a tissue by a gel can be varied at will, and behaves in a reasonable and predictable way. Although the gel compositions in this example were degradable, the peeling was done at short times, and the results will extrapolate directly to non-degradable gels.

In the following Examples 29–30, the following methods and parameters were used:

Elongation to Fracture and Young's or Other Elastic Modulus

Samples are prepared in a mold to have the required concentration of monomer and other ingredients. The crosslinked or otherwise cured specimens are placed in an appropriate machine, such as an Instron™ tester, and the force required to stretch the sample along a single axis is measured as a function of the distance the sample is stretched (strain). Elongation may be continued until the sample breaks, giving the value for elongation at break, optionally after cycling at lower elongations to determine the degree of any plastic deformation of the sample. The data (force vs. distance) may be recorded and used to make a plot, as in FIG. 1. Because the response of a particular material is not necessarily "ideal", especially at high elongation, a modulus may be calculated from values at low degrees of elongation where the behavior is closer to linear. Alternatively, the force vs. strain values may be used directly without extrapolation, or without division by sample thickness to give the "normalized compliance" discussed above.

Bulk Compression Modulus

The sample of gel or tissue is placed in a suitable instrument, such as a Perkin-Elmer DMA 7e, and the modulus is measured according to a standard procedure. A gel sample could also be polymerized directly in the instrument for testing.

Adhesive Strength

This was tested by a lap shear test. The test sealant material was used to adhere a 1 cm×1 cm area of two pieces of test substrate, typically a standardized tissue such as rat peritoneum or pig pericardium. After crosslinking or curing of the test material, the force required to break the adhesive bond was determined using a suitable instrument, such as an Instron™ tester. In one variant of the test, three pieces of substrate were adhered: a center piece, with tab extending in one direction, and a pair of outer pieces with tabs extending in the opposite direction; sealant was used to join all three pieces. Either arrangment also can be used to determine the relative mechanical properties of various samples (i.e., compared to standards) at small displacements, which is useful when only limited sample volume is available.

Adherence

Adherence of sealant formulae in vivo is determined qualitatively, by the relative resistance of the sealant to displacement from its deposition site by a probe.

Viscosity

Viscosity was measured by standard methods, typically in a Brookfield™ viscometer.

Seal Pressure Testing

Seal Pressure Testing was performed by punching a 3 mm round hole in a standard tissue, such as pig pericardium, and mounting the tissue as the closure in a test fixture. Sealant was applied to the hole and cured, typically in a spiral pattern, to obtain closure of the hole. Then increasing pressure was applied to the transverse side of the tissue until the plug of sealant was displaced.

Sealant Polymerization

In Examples 29–30 below, a preferred formulation of the sealing system was used. When applied to tissue or to a surface to which adherence was required, the surface was primed with a mixture which contained by weight approximately 65% water, 30.4% of a polymerizable macromer (3.3KL5A2, a 3.5 kD polyethylene glycol backbone carrying an average of 5 lactate groups and end capped with acrylate), 3% NaCl, 1% fructose, 0.5% ferrous gluconate, and 0.2% Eosin Y. The primer was applied to the surface and spread with a brush. Then about 2 volumes of sealant solution was applied and mixed with a brush. The sealant contained about 77% water, 20.5% polymerizable macromer 35KTM8A2 (35 kD polyethylene glycol carrying an average of 8 trimethylenecarbonate groups and end capped with acrylate), 1.1% triethanolamine, 1%KH2PO4, 0.4% vinylcaprolactam, 0.013% t-butyl hydroperoxide, and 0.002% Eosin Y. When the sealant solution was tested in isolation, the t-butyl hydroperoxide was omitted. The sealant system was photopolymerized by exposure to blue-green light for about 40 sec.

EXAMPLE 29

Elasticity Results

Using the materials described above, lap shear testing samples were prepared by applying the macromer solution with a cotton swab to a 1 cm×1 cm area on a 3 cm×1 cm strip of rat peritoneal tissue, then laying the other strip of the same size on top as to make a sandwich. The sample was then transilluminated from the top and then the bottom for 40 sec each. Lap shear testing was performed using a 12.5 mm gauge length. Tensile testing using a sample size of 45 mm×10 mm×5 mm and a 12.5 mm gauge length, was performed. DMA (Perkin Elmer) testing with a sample height of 1.6 mm was performed at 37° C. after hydrating for 2 hours in saline at 37° C. A subjective scoring system was used to assess adherence in a goat lung model on a scale from 1–4 (1=poor adherence & 4=excellent adherence).

In Vitro Testing

This synthetic surgical sealant could be rapidly polymerized with visible light to form a flexible hydrogel. As can be seen from the tensile data in FIG. 1, this material showed a completely elastic deformation profile with linear elongation at break in excess of 700%. The polymerization process of this material and the properties of lung tissue and muscle tissue were studied using the dynamic mechanical tester. It was seen that muscle tissue, as expected, had a higher modulus than spongy parenchymal lung tissue. The sealant material was cured within 40 seconds and reached a final modulus very comparable to that of the lung tissue. This ensures a compliant and persistent adhesive bond. The bond strength was determined using the lap shear test apparatus and the material was seen to form a strong yet flexible bond to tissue. This bond strength is in excess of literature values for fibrin glues in comparable tests. Table 1 shows a summary of in vitro results.

In Vivo Testing

All goats that had undergone the thoracotomy procedure survived the surgery uneventfully. Goats were sacrificed at timepoints of 14 days, 1 month, and 3 months. At all timepoints, the hydrogel was seen to be firm and clear and had an adherence score of 3.0–3.5 out of 4.0. No tissue necrosis was evident. Histological sections of the tissue showed normal healing. The results are shown below in Table 2.

Table 2

In-Vitro Testing Summary
Property; Result
Compressive modulus at full cure, sealant; 32.4 kPa
Compressive modulus of lung tissue, pig; 27.5±3.4 kPa
Compressive modulus of lung tissue, dog; 28.0±1.9 kPa
Modulus of rat muscle tissue; 73.4±6.8 kPa
Young's modulus at full cure, sealant; 29.4 kPa
Elongation at break, sealant; 788±255.2%
Sealant lap shear strength; 90.17±18.17 g/cm$^2$

EXAMPLE 30

Comparative Results

Tissucol™ sealant is a commercial fibrin sealant used in Europe. It is not at present approved for use in the United States, in part because it is made from human serum and thus may carry infectious agents. Tissucol sealant was used according to its manufacturer's directions. In comparison to the preferred sealant formulation of the previous example, the following results were obtained shown in Table 3:

Table 3

Properties of Sealants

TABLE 3

Properties of Sealants

| Test: | FocalSeal ™ Sealant | Tissucol ™ Sealant |
|---|---|---|
| A. Double lap shear | 38 ± 6 kPa | 10 ± 6 kPa |
| B. Compression Modulus | 32 ± 1 kPa | 35 ± 5 kPa |
| C. Viscosity | ≈780 cP at 20% conc. | 117 cP (fibrinogen) 1.6 CP (thrombin) |
| D. Seal Pressure Test | ≈380 ± 100 mm Hg | ≈30 ±20 mm Hg |

When applied to a living dog lung, the fibrin sealant had an adhesion score of 1, and leaked on all staple lines at 10–40 mm Hg. It was difficult to apply the fibrin material to a punch-type leak, because air bubbles coming through the leak tended to remove the material before it polymerized. In contrast, sealant adhered to primed tissue with an adhesion of 3.5, and typically withstood 80 mm Hg or more of pressure. Its high viscosity slowed bubble penetration.

The optimal material for lung, as described above, has an elongation at break of over 700%. Other materials were suitable, if less optimal. For non-collapsed lung, a material (20KT8A2) with an elongation at break of 225% was suitable, while a material (8KL5A2) with an elongation at break of 100% (and an elastic modulus of 47±4 kPa) was not effective in lung. The expansion of a dog lung was measured. It was found that the effective area expansion during a normal breathing cycle is about 200%, while the expansion from the atalectatic (collapsed) state to full inflation changed area by about 300%. In the latter case, an extension (strain) of about 100% was observed along one axis, and about 200% along a perpendicular axis, implying non-uniformity of the tissue structure.

Thus, an important requirement for a sealant system on this tissue appears to be that the normalized compliance of the sealant is greater than the normalized compliance of the tissue to which it is applied. While the lung is perhaps the most dramatic example of tissue elasticity and area expansion during normal physiological processes, other tissues, such as the bowels, the bladder and large arteries, can change surface area substantially during normal physiological cycles. Other tissues, such as the beating heart, exhibit significant changes in shape (shear) without necessarily changing local area.

The compliance of the sealant may be selected depending on the tissue to which it is to be applied. A sealant having a high value of normalized compliance, or a low value of the normalized compliance ratio (tissue /material), may be beneficial for certain applications. For example, the 700%—elongation low-modulus material described above is also suitable for sealing the dura of the brain, or the spinal cord after laminectomy, even though these tissues are relatively non-compliant (i.e., are difficult to stretch). Thus, high normalized compliance sealant appears to be useful on most tissues, and desirable as a material having a broad range of applications.

What is claimed is:

1. A compliant polymeric material on a tissue surface, wherein the material is formed by the polymerization of an aqueous solution or suspension of a polymerizable monomer in contact with the tissue surface, and
    wherein the normalized compliance ratio of the tissue and the material is in the range of about 0.05 to about 3.
2. The material of claim 1 wherein the compliant material is a hydrogel,
    wherein the monomer is a photopolymerizable, biodegradable, water-soluble block copolymer comprising photopolymerizable groups, and
    wherein the monomer is polymerized in the presence of a free radical polymerization initiator.
3. The material of claim 1 wherein the polymerized material has an elongation at rupture which is similar to or greater than the elongation of the tissue in vivo.
4. The material of claim 1 wherein the polymerized material has an elongation at rupture which is greater than about 100%.
5. The material of claim 1 wherein the polymerized material has an elastic modulus which is less than about 150 kPa.
6. The material of claim 1 wherein the material has an adherence to the surface of at least about 20 grams per square centimeter.
7. The material of claim 1 wherein the material further comprises a biologically active material.
8. The material of claim 1, wherein the material is biodegradable.
9. The material of claim 1 wherein the material forms a sealant on a tissue surface.
10. The material of claim 1 wherein the material adheres two surfaces together, and wherein at least one of the surfaces is a tissue surface.

11. A kit for the preparation of the compliant material of claim 1, comprising one or more containers each containing one or more of a polymerizable monomer, a priming material and an initiator of polymerization.

12. A method for forming a compliant polymeric material on a tissue surface, the method comprising applying an aqueous solution or suspension of a polymerizable monomer to the surface; and polymerizing the material on the surface;

wherein the normalized compliance ratio of the tissue and the material is in the range of about 0.05 to about 3.

13. The method of claim 12 wherein the material further forms a sealant on the tissue surface.

14. The method of claim 13 wherein the monomer is a photopolymerizable, biodegradable, water-soluble block copolymer comprising photopolymerizable groups, and wherein the method comprises photopolymerizing the monomer on the tissue surface in the presence of a free radical polymerization initiator.

15. The method of claim 12 wherein the polymerized material has an elongation at rupture which is similar to or greater than the elongation of the tissue in vivo.

16. The method of claim 12 wherein the polymerized material has an elongation at rupture which is greater than about 100%.

17. The method of claim 12 wherein the polymerized material has an elastic modulus which is less than about 150 kPa.

18. The method of claim 12 wherein the material has an adherence to the surface of at least about 20 grams per square centimeter.

19. The method of claim 12 wherein the material further comprises a biologically active material.

20. The method of claim 12, wherein the material is biodegradable.

21. The method of claim 19 wherein the method comprises applying the polymerizable monomer and the biologically active material to the surface of a biological tissue and polymerizing the monomer on the tissue to form a polymeric compliant material on the surface incorporating the biologically active material, wherein the material is capable of controlled release of the biologically active material.

22. The method of claim 12 wherein the polymerizable monomer is applied to a plurality of surfaces, at least one of said surfaces being a tissue surface, and wherein the polymerization of the material on the surface causes adhering of the surfaces.

23. The method of claim 13 wherein the compliant polymeric material is formed on the surface of a lung in vivo.

* * * * *